(12) United States Patent  (10) Patent No.: US 7,638,663 B2
Egawa et al.  (45) Date of Patent: Dec. 29, 2009

(54) STILBENE DERIVATIVE, LIGHT EMITTING ELEMENT MATERIAL, LIGHT EMITTING ELEMENT, LIGHT EMITTING DEVICE AND ELECTRONIC APPLIANCE

(75) Inventors: Masakazu Egawa, Tochigi (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 449 days.

(21) Appl. No.: 11/591,759

(22) Filed: Nov. 1, 2006

(65) Prior Publication Data

US 2007/0100180 A1    May 3, 2007

(30) Foreign Application Priority Data

Nov. 3, 2005   (JP)   ............... 2005-320228

(51) Int. Cl.
C07C 15/30  (2006.01)
C09K 11/06  (2006.01)
H01L 51/54  (2006.01)

(52) U.S. Cl. .................. 585/26; 428/690; 428/917; 313/504; 313/506

(58) Field of Classification Search .................. None
See application file for complete search history.

(56) References Cited

U.S. PATENT DOCUMENTS 7,476,745 B2   1/2009  Egawa et al.
2005/0175858 A1  8/2005  Jung et al.

FOREIGN PATENT DOCUMENTS

JP    05-295359    11/1993
JP   2004-035447    2/2004
JP   2005-132820    5/2005

*Primary Examiner*—Dawn Garrett
(74) *Attorney, Agent, or Firm*—Cook Alex Ltd.

(57) ABSTRACT

An object of the present invention to provide a novel stilbene derivative having a large energy gap. In addition, it is another object of the present invention to provide a novel light emitting element material having a large energy gap which is suitable for a host material in a light emitting layer. Further in addition, it is another object of the present invention to provide a novel light emitting element material having a large energy gap and an electron transporting property. The present invention provides a stilbene derivative represented by a following general formula (3) and a light emitting element material including the stilbene derivative represented thereby:

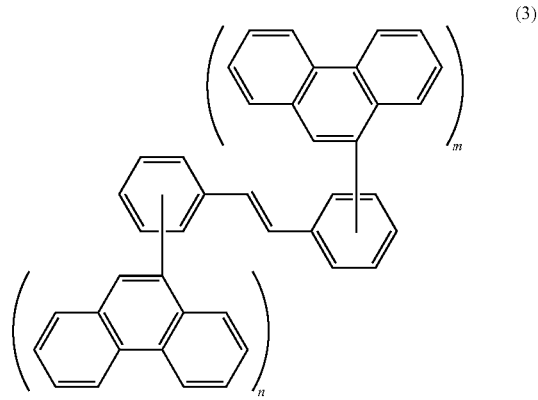

wherein, n is an integer of 0 or more and 2 or less and m is an integer of 1 or more and 2 or less.

20 Claims, 19 Drawing Sheets

STILBENE DERIVATIVE, LIGHT EMITTING ELEMENT MATERIAL, LIGHT EMITTING ELEMENT, LIGHT EMITTING DEVICE AND ELECTRONIC APPLIANCE

BACKGROUND OF THE INVENTION

1. Field of the Invention

The present invention relates to a novel material. In particular, the present invention relates to a material which is preferably used in a light emitting element in which an organic compound is used in at least one part. In addition, the present invention relates to a light emitting element, a light emitting device, and an electronic appliance which include the material.

2. Description of the Related Art

Development of a light emitting device using a light emitting element which includes an organic compound containing layer between a pair of electrodes and emits light when current flows between the electrodes has been advanced. Such a light emitting device has the advantage of being thin and lightweight, compared with other display devices at present which are called thin display devices. Such a light emitting device also has high visibility since it is a self-light emitting element, and has fast response speed. Therefore, this kind of light emitting device has been actively developed as a next-generation display device, and has partly come into practical use.

A light emitting mechanism of the light emitting element is described below. When a voltage is applied between a pair of electrodes, electrons injected from a cathode and holes injected from an anode recombine with each other to form molecular excitons in a light emitting layer included in an organic compound containing layer. The molecular exciton releases energy when returning to a ground state, so that light is emitted. Singlet excitation and triplet excitation are known as excited states, and it is thought that light emission can be achieved through each of the excited states.

The organic compound containing layer provided between the electrodes may have either a single-layer structure including one light emitting layer or a stacked-layer structure including layers having different functions from each other; however, the latter, a stacked-layer structure of a function-separated type, is often employed. As an example of such a stacked-layer structure of a function-separated type, a structure where a hole injection layer, a hole transport layer, a light emitting layer, and an electron injection layer are sequentially stacked over an electrode serving as an anode is typical, and each layer is formed of a material specific to each function. Note that a layer having two or more kinds of these functions such as a layer having both functions of a light emitting layer and an electron transport layer or a layer having another function such as a carrier blocking layer may be used.

Among the foregoing functional layers, a light emitting layer can be roughly classified into two types according to its structure. One is a structure in which a light emitting layer is a single film of a light emitting substance. The other is a structure in which a light emitting layer is formed by dispersing a light emitting substance in a host material. The latter structure is advantageous since in the latter structure, a light emitting substance can be selected without depending on a crystalline property and a film forming property thereof, and concentration quenching is hardly caused.

In the case of using such a light emitting layer having a structure in which a light emitting substance is dispersed in a host material, the host material needs to have a larger energy gap than the light emitting substance. This is an important requirement aiming at prevention of changes in light emission efficiency and light emission color due to excitation energy of an excited light emitting substance moving to the host material, and aiming at improvement in light emission efficiency due to the excitation energy moving smoothly from the excited host material to the light emitting substance.

A color of light emitted from a light emitting substance depends on an energy gap of the light emitting substance. The larger energy gap a light emitting substance has, the shorter wavelength of light is emitted. Therefore, a host material used with a light emitting substance exhibiting blue light emission needs to have a very large energy gap. However, there have not been many of such materials yet (for example, see Patent Document 1). Further, a host material used with a light emitting substance exhibiting violet or ultraviolet light emission is required to have an even larger energy gap.

When a light emitting element is manufactured using the foregoing stacked-layer structure of a function-separated type, each functional layer is formed of a material suitable for each function. To obtain a high-performance light emitting element, each functional layer thereof is required to have excellent characteristics in every aspect. However, an electron transporting material for forming an electron transport layer has been less reported compared to a hole transport material for forming a hole transporting layer, and there has been a delay in development of the electron transporting material under the present condition.

For example, tris(8-quinolinolato)aluminum (abbr.: $Alq_3$) which is widely used as an electron transporting material has an excellent electron transporting property and reliability. However, since its emitting color is green, it is understood that an energy gap of $Alq_3$ is small. Therefore, in a light emitting element which emits light with wavelength of blue or shorter, $Alq_3$ is difficult to be used as an electron transport layer being in contact with a light emitting layer. This is because when a light emitting region in a light emitting layer is closer to an electron transport layer side, excitation energy of a light emitting substance and a host material moves to the electron transport layer side which has a small energy gap.

To avoid such a problem, it is efficient to use an electron transporting material as a host material and to set a light emitting region in a light emitting layer closer to an hole transport layer side. However, as described above, an electron transporting material has been less reported and there are a very small number of electron transporting materials which can be used as a host material in a light emitting element which emits light with wavelength of blue or shorter.

[Patent Document 1] Japanese Published Patent Application No. 2005-132820

SUMMARY OF THE INVENTION

In accordance with the foregoing problems, it is an object of the present invention to provide a novel stilbene derivative having a large energy gap. In addition, it is another object of the present invention to provide a novel light emitting element material which is suitable for a host material in a light emitting layer. Further in addition, it is another object of the present invention to provide a novel light emitting element material having a large energy gap and an electron transporting property.

Further, it is another object of the present invention to provide a light emitting element with favorable color purity and emission efficiency, which includes either the foregoing stilbene derivative or light emitting element material.

Further, it is another object of the present invention to provide a light emitting device with a high display quality and low power consumption, which includes either the foregoing stilbene derivative or light emitting element material.

Still further, it is another object of the present invention to provide an electronic appliance with low power consumption, which has a light emitting device with a high display quality including either the foregoing stilbene derivative or light emitting element material.

The present invention is a stilbene derivative represented by a following general formula (1).

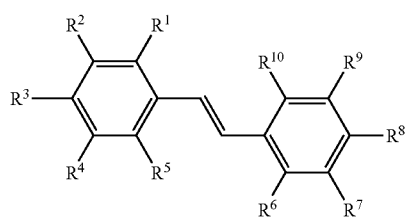

(1)

In the formula, each of $R^1$, $R^2$, $R^3$, $R^4$, and $R^5$ represents hydrogen or a substituent represented by a following structural formula (2), and at least one of $R^1$, $R^2$, $R^3$, $R^4$, or $R^5$ is the substituent represented by the following structural formula (2); and each of $R^6$, $R^7$, $R^8$, $R^9$, and $R^{10}$ represents hydrogen or the substituent represented by the following structural formula (2), and at least one of $R^6$, $R^7$, $R^8$, $R^9$, or $R^{10}$ is the substituent represented by the following structural formula (2).

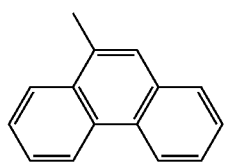

(2)

The present invention is a stilbene derivative represented by a following general formula (3).

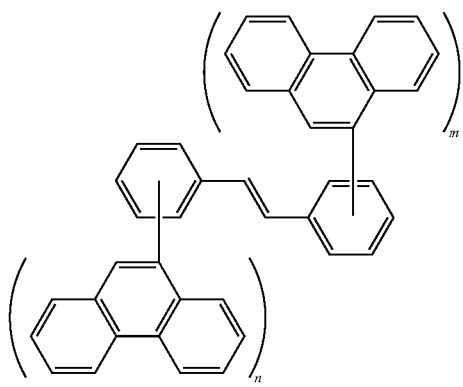

(3)

In the formula, n is an integer of 0 or more and 2 or less and m is an integer of 1 or more and 2 or less. Note that a structure is preferable in which n=1 and m=2.

The present invention is a stilbene derivative represented by a following structural formula (4).

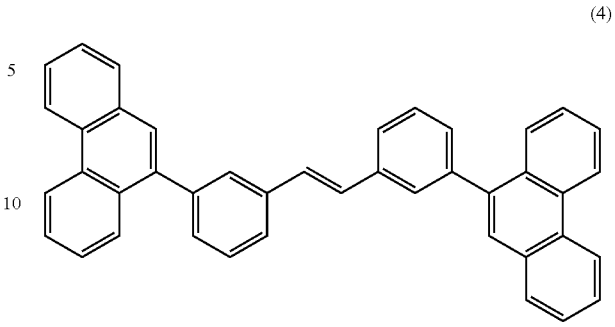

(4)

The present invention is a stilbene derivative represented by a following structural formula (5).

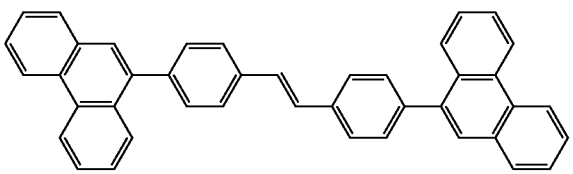

(5)

The present invention is a light emitting element material having any one of the foregoing stilbene derivatives.

The present invention is a light emitting element having any one of the foregoing stilbene derivatives.

The present invention is a light emitting device having the foregoing light emitting element and a control circuit controlling light emission of the light emitting element.

The present invention is an electronic appliance which has a display portion including the foregoing light emitting element and a control circuit controlling the light emitting element.

A stilbene derivative of the present invention is a novel material having a large energy gap. In addition, a stilbene derivative of the present invention is a novel material having an electron transporting property and a large energy gap. A light emitting element material of the present invention has a large energy gap and is a novel light emitting element material especially suitable as a host material of a light emitting layer. In addition, a light emitting element material of the present invention is a novel light emitting element material having a large energy gap and an electron transporting property.

A light emitting element of the present invention is a light emitting element with favorable color purity and light emission efficiency.

A light emitting device of the present invention is a light emitting device with a high display quality and low power consumption.

An electronic appliance of the present invention is an electronic appliance with low power consumption, which has a light emitting device with a high display quality.

DETAILED DESCRIPTION OF THE INVENTION

Figure 1:
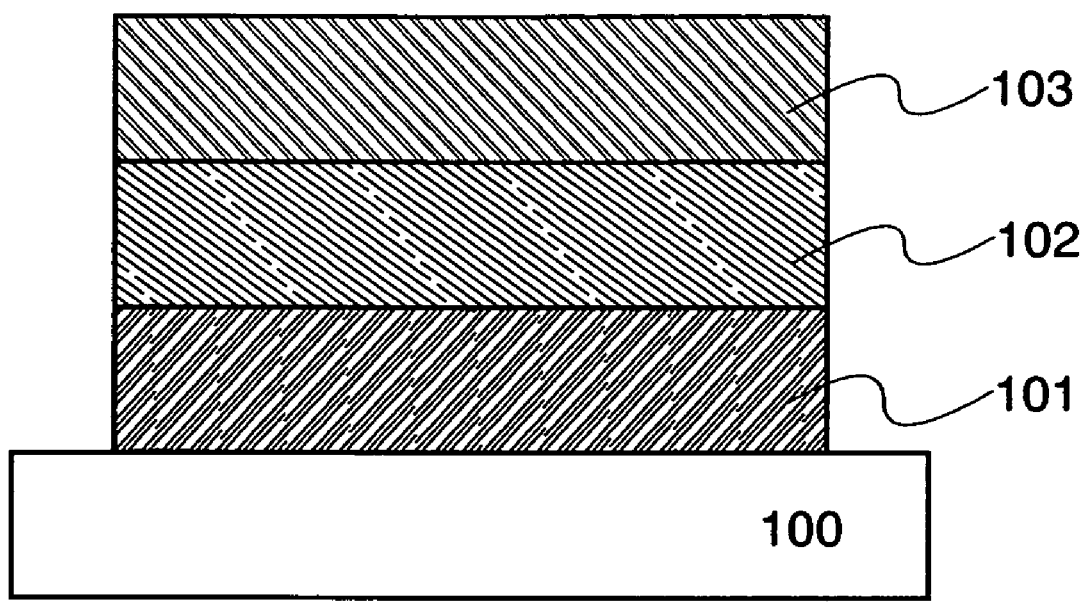
FIG. 1 shows a light emitting element of the present invention.

Hereinafter, the embodiment modes of the present invention will be described with reference to the accompanying drawings. The present invention can be carried out in many different modes, and it is easily understood by those skilled in the art that modes and details herein disclosed can be modified in various ways without departing from the purpose and the scope of the present invention. Accordingly, the present invention should not be interpreted as being limited to the description of the embodiment modes to be given below.

Embodiment Mode 1

A stilbene derivative of the present invention is described in this embodiment mode.

A stilbene derivative of the present invention is represented by a following general formula (1).

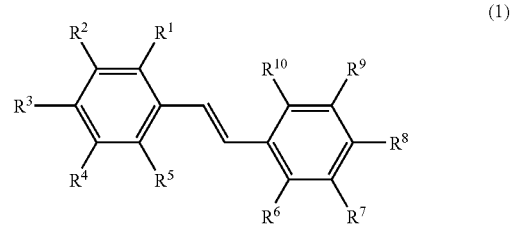

(1)

In the general formula (1) each of $R^1$, $R^2$, $R^3$, $R^4$, and $R^5$ represents hydrogen or a substituent represented by a following structural formula (2), at least one of $R^1$, $R^2$, $R^3$, $R^4$, or $R^5$ is the substituent represented by the following structural formula (2). In addition, in the general formula (1), each of $R^6$, $R^7$, $R^8$, $R^9$, and $R^{10}$ represents hydrogen or the substituent represented by the following structural formula (2), and at least one of $R^6$, $R^7$, $R^8$, $R^9$, or $R^{10}$ is the substituent represented by the following structural formula (2).

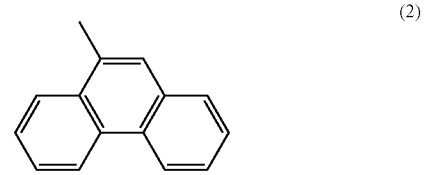

(2)

The substituent represented by the foregoing structural formula (2) may have another substituent, such as an alkyl group, a haloalkyl group, an alkoxy group, an acyl group, an alkoxycarbonyl group, an acyloxy group, a halogen group, or an aryl group. Specifically, as an alkyl group, a methyl group, an ethyl group, and the like are given. As a haloalkyl group, a trifluoromethyl group, and the like are given. As an alkoxy group, a methoxy group and the like are given. As an acyl group, an acetyl group and the like are given. As an alkoxycarbonyl group, a methoxycarbonyl group, and the like are given. As an acyloxy group, an acetoxy group and the like are given. As a halogen group, a fluoro group and the like are given. As an aryl group, a phenyl group, a biphenyl group, a naphthyl group, and the like are given.

A stilbene derivative of the present invention is represented by the following general formula (3).

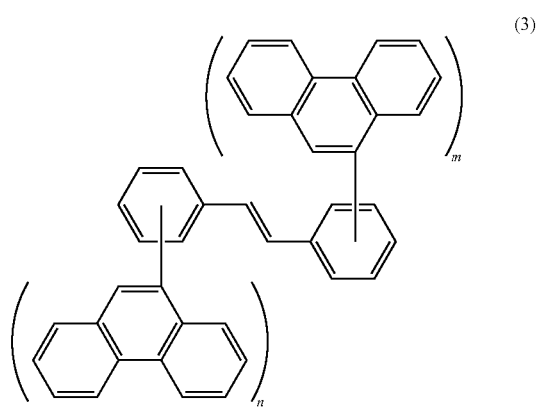

(3)

In the general formula (3), n is an integer of 0 or more and 2 or less and m is an integer of 1 or more and 2 or less. A structure where n=1 and m=2 is preferable.

A stilbene derivative of the present invention is represented by the following structural formula (4).

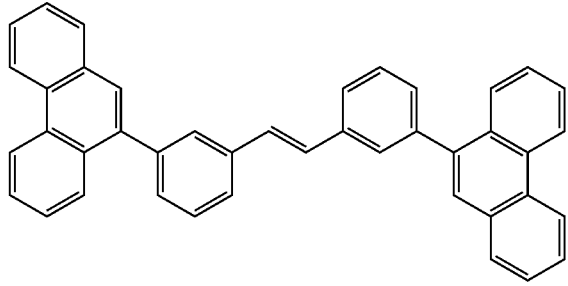

(4)

A stilbene derivative of the present invention is represented by the following structural formula (5).

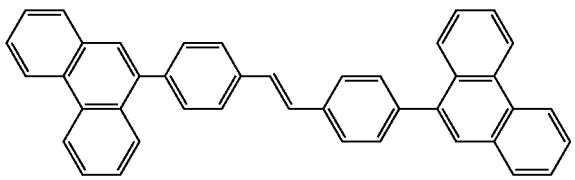

(5)

A stilbene derivative of the present invention having the foregoing structure is a material having a large energy gap. By using a stilbene derivative of the present invention as a host material of a light emitting layer in an organic compound containing layer of a light emitting element, even if a substance exhibiting blue light emission is used as a light emitting substance, excitation energy does not move to the host material from the light emitting substance, and a light emitting element with high emission efficiency and color purity can be manufactured.

In addition, a stilbene derivative of the present invention with the foregoing structure has an electron transporting property. Therefore, by using a stilbene derivative of the present invention as a host material of a light emitting layer in an organic compound containing layer of a light emitting element, a light emitting region can be prevented from being closer to the electron transport layer side in which the range of choice of a material is narrow. Therefore, a light emitting element with high emission efficiency and color purity is easily designed and a light emitting element with high emission efficiency and color purity can be manufactured.

In addition, a stilbene derivative of the present invention with the foregoing structure is a material having a large energy gap and an electron transporting property. By using a stilbene derivative of the present invention as a host material of a light emitting layer in an organic compound containing layer of a light emitting element, even if a substance exhibiting blue light emission is used as a light emitting substance, excitation energy does not move to a host material from the light emitting substance, so that a light emitting element is easily designed and a light emitting element with high emission efficiency and color purity can be manufactured.

Note that a stilbene derivative of the present invention having the foregoing structure can be applied not only to a light emitting element exhibiting blue light but a light emitting element exhibiting red or green light emission with wavelength longer than blue. Note that a wavelength region of light emission of a stilbene derivative of the present invention and a wavelength region of light absorption of a light emitting substance preferably overlaps each other so that excitation energy moves from the stilbene derivative of the present invention to the light emitting substance smoothly.

In addition, a stilbene derivative of the present invention can be used as a host material of a light emitting element exhibiting light with a wavelength region shorter than blue (violet to ultraviolet light) when a light emitting substance has an energy gap smaller than that of the stilbene derivative described in Embodiment Mode 1. A stilbene derivative of the present invention has a very large energy gap and can be favorably used as a host material to be used with a light emitting substance exhibiting light emission with a wavelength region from violet to ultraviolet light.

Embodiment Mode 2

A light emitting element using the stilbene derivative described in Embodiment Mode 1 is described in this embodiment mode.

A light emitting element of the present invention has a structure in which an organic compound containing layer is interposed between a pair of electrodes. Note that there is no particular limitation on an element structure, and a structure can be appropriately selected for the purpose.

FIG. 1 shows an example of frame format of an element structure of a light emitting element of the present invention. The light emitting element shown in FIG. 1 has a structure in which an organic compound containing layer 102 is interposed between a first electrode 101 and a second electrode 103, over an insulator 100. The organic compound containing layer 102 contains the stilbene derivative described in Embodiment Mode 1. An anode in the present invention refers to an electrode which injects holes into a layer containing a light emitting substance. On the other hand, a cathode in the present invention refers to an electrode which injects electrons into a layer containing a light emitting substance. One of the first electrode 101 and the second electrode 103 serves as an anode, and the other serves as a cathode.

For the anode, a metal, an alloy, a conductive compound, a mixture thereof, or the like having a high work function (specifically, 4.0 eV or higher) is preferably used. Specifically, indium tin oxide (hereinafter referred to as ITO), indium tin oxide containing silicon, indium oxide containing zinc oxide (ZnO), or the like can be given. These conductive metal oxide films are generally formed by a sputtering method, but may be formed by a sol-gel method or the like. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (for example, titanium nitride (TiN)), or the like can be used.

On the other hand, for the cathode, a metal, an alloy, a conductive compound, a mixture thereof, or the like having a low work function (specifically, 3.8 eV or lower) is preferably used. Specifically, metal belonging to Group 1 or 2 of the periodic table, that is, alkali metal such as lithium (Li) or cesium (Cs); alkaline earth metal such as magnesium (Mg), calcium (Ca), or strontium (Sr); or an alloy containing these metals (MgAg, AlLi, or the like) can be given. Alternatively, rare-earth metal such as europium (Er) or ytterbium (Yb), an alloy containing these, or the like can be given. Note that when using an electron injection layer having a high electron injecting property, the cathode can also be formed using a material having a high work function, that is, a material generally used for the anode. For example, the cathode can be formed of metal or a conductive inorganic compound such as Al, Ag, or ITO.

The organic compound containing layer 102 can be formed using either a low molecular material or a high molecular material. Note that, a material forming the organic compound containing layer 102 is not limited to a material containing only an organic compound material, and it may partially contain an inorganic compound material. In addition, the organic compound containing layer 102 may be formed by appropriately combining functional layers having respective functions, such as a hole injection layer, a hole transport layer, a hole blocking layer, a light emitting layer, an electron transport layer, and an electron injection layer. The functional layers may include a layer having two or more functions at the same time. In this embodiment mode, a stacked-layer structure including a hole injection layer, a hole transport layer, a light emitting layer, an electron transport layer, and an electron injection layer is employed. Note that a light emitting layer in this embodiment mode is formed by dispersing a light emitting substance in a host material containing the stilbene derivative described in Embodiment Mode 1. Therefore, concentration quenching can be further prevented compared to when a light emitting layer is formed by a film only containing a light emitting substance.

In addition, the organic compound containing layer 102 can be formed by either a wet method or a dry method such as an evaporation method, an ink-jet method, a spin coating method, or a dip coating method.

The stilbene derivative described in Embodiment Mode 1 having the foregoing structure is a material having a large energy gap. A light emitting element of the present invention contains the stilbene derivative described in Embodiment Mode 1 as a host material of a light emitting layer in the organic compound containing layer 102 of a light emitting element. Even if a substance exhibiting blue light emission is used as a light emitting substance, excitation energy does not move to the host material from the light emitting substance. Therefore, a light emitting element of the present invention can be a light emitting element with high emission efficiency and color purity.

In addition, the stilbene derivative described in Embodiment Mode 1 has an electron transporting property. In a light emitting element of the present invention, the stilbene derivative described in Embodiment Mode 1 is used as a host material of a light emitting layer in the organic compound containing layer 102 of a light emitting element. Therefore, a light emitting region can be prevented from being closer to the electron transport layer side in which the range of choice of a material is narrow. Therefore, a light emitting element with high emission efficiency and color purity is easily designed and a light emitting element of the present invention can be a light emitting element with high emission efficiency and color purity.

In addition, the stilbene derivative described in Embodiment Mode 1 is a material having a large energy gap and an electron transporting property. In a light emitting element of the present invention, the stilbene derivative described in Embodiment Mode 1 is used as a host material of a light emitting layer in the organic compound containing layer 102 of a light emitting element. Therefore, even if a substance exhibiting blue light emission is used as a light emitting substance, excitation energy does not move to a host material from the light emitting substance, so that a light emitting element is easily designed and a light emitting element of the present invention can be a light emitting element with high emission efficiency and color purity.

Note that a light emitting element of the present invention can be applied not only to a light emitting element exhibiting blue light but a light emitting element exhibiting red or green light emission with wavelength longer than blue. Note that a wavelength region of light emission of a host material and a wavelength region of light absorption of a light emitting substance preferably overlaps each other so that excitation energy moves from the host material to the light emitting substance smoothly.

In addition, a light emitting element of the present invention can be used as a host material of a light emitting element exhibiting light with a wavelength region shorter than blue (violet to ultraviolet light) when a light emitting substance has an energy gap smaller than that of the stilbene derivative described in Embodiment Mode 1. The stilbene derivative described in Embodiment Mode 1 has a significantly large energy gap, so that the stilbene derivative described in Embodiment Mode 1 can be favorably used as a host material to be used with a light emitting substance exhibiting light emission with a wavelength region from violet to ultraviolet light.

The hole injection layer can be formed of metal oxide such as vanadium oxide, molybdenum oxide, ruthenium oxide, aluminum oxide, or a compound in which an appropriate organic compound is mixed with the foregoing metal oxide. Alternatively, a porphyrin-based compound is effective among organic compounds, and phthalocyanine (abbr.: $H_2Pc$), copper phthalocyanine (abbr.: CuPc), or the like can be used. Further, a chemically-doped conductive high molecular compound can be used, such as polyethylene dioxythiophene (abbr.: PEDOT) or polyaniline (abbr.: PAni) each of which is doped with polystyrene sulfonate (abbr.: PSS). The hole injection layer is formed to be in contact with the anode, By providing the hole injection layer, a carrier injection barrier can be lowered and carriers are efficiently injected into the light emitting element; as a result, a drive voltage can be reduced.

The hole transport layer can be formed of an appropriate material such as N,N'-bis(spiro-9,9'-bifluorene-2-yl)-N,N'-diphenylbenzidine (abbr.: BSPB), 4,4'-bis[N-(1-naphthyl)-N-phenylamino]biphenyl (abbr.: NPB), 4,4'-bis[N-(3-methylphenyl)-N-phenylamino]biphenyl (abbr.: TPD), 4,4',4"-tris (N,N-diphenylamino)triphenylamine (abbr.: TDATA), 4,4', 4"-tris[N-(3-methylphenyl)-N-phenylamino]triphenylamine (abbr.: MTDATA), 4,4'-bis{N-[4-(N,N-di-m-tolylamino) phenyl]-N-phenylamino}biphenyl (abbr.: DNTPD), 1,3,5-tris[N,N-di(m-tolyl)amino]benzene (abbr.: m-MTDAB), 4,4',4"-tris(N-carbazolyl)triphenylamine (abbr.: TCTA), phthalocyanine (abbr.: $H_2Pc$), copper phthalocyanine (abbr.: CuPc), or vanadyl phthalocyanine (abbr.: VOPc). In addition, a hole transport layer may have a multilayer structure in which two or more layers formed of the foregoing substance are combined.

The light emitting layer is formed by dispersing a light emitting substance in a host material containing the stilbene derivative described in Embodiment Mode 1. A substance which has favorable light emission efficiency and can emit light with desired emission wavelength may be used as the light emitting substance. For example, in order to obtain red light emission, a substance which exhibits light emission having a peak of an emission spectrum at 600 to 680 nm can be used, such as 4-dicyanomethylene-2-isopropyl-6-[2-(1,1, 7,7-tetramethyljulolidin-9-yl)ethenyl]-4H-pyran (abbr.: DCJTI), 4-dicyanomethylene-2-methyl-6-[2-(1,1,7,7-tetramethyljulolidin-9-yl)ethenyl]-4H-pyra n (abbr.: DCJT), 4-dicyanomethylene-2-tert-butyl-6-[2-(1,1,7,7-tetramethyljulolidin-9-yl)ethenyl]-4H-py ran (abbr.: DCJTB), periflanthene, or 1,4-bis[2-(10-methoxy-1,1,7,7-tetramethyljulolidin-9-yl)ethenyl]-2,5-dicyano benzene. In order to obtain green light emission, a substance which exhibits light emission having a peak of an emission spectrum at 500 to 550 nm can be used, such as N,N'-dimethylquinacridon (abbr.: DMQd), coumarin 6, coumarin 545T, or tris(8-quinolinolato) aluminum (abbr.: $Alq_3$). In order to obtain blue light emission, a substance which exhibits light emission having a peak of an emission spectrum at 420 to 500 nm can be used, 2,5,8,11-tetra(tert-butyl)perylene (abbreviation: TBP), 9,10-di(2-naphthyl)-tert-butylanthracene (abbr.: t-BuDNA), 9,9'-bianthryl, 9,10-diphenylanthracene (abbr.: DPA), 9,10-di(2-naphthyl)anthracene (abbr.: DNA), bis(2-methyl-8-quinolinolato)-4-phenylphenolato-gallium (abbr.: BGaq), or bis(2-methyl-8-quinolinolato)-4-phenylphenolato-aluminum (abbr.: BAlq). In order to obtain light emission in a wavelength region from violet to ultraviolet light, TPD, m-MTDATA, 4,4'-bis[N-(biphenyl-4-yl)-N-phenylamino]biphenyl (abbr.: BBPB), 2,2',7,7'-tetrakis(N-diphenylamino)-spiro-9,9'-bifluorene (abbr.: spiro-TAD), 1,3,5-tris[N,N-bis(2-methylphenyl)amino]benzene (o-MTDAB), or the like can be used. In addition to the foregoing substances which exhibit fluorescence, substance which exhibits phosphorescence can also be used as a light emitting material, such as bis[2-(3',5'-bis(trifluoromethyl)phenyl)pyridinato-N,$C^{2'}$]iridium(III)picolinate (abbr.: $Ir(CF_3ppy)_2(pic)$), bis[2-(4',6'-difluorophenyl)pyridinato-N,$C^{2'}$]iridium(III)acetylacetonate (abbr.: FIr(acac)), bis[2-(4',6'-difluorophenyl)pyridinato-N, $C^{2'}$]iridium(III)picolinate (abbr.: FIr(pic)), or tris(2-phenylpyridinato-N,$C^{2'}$)iridium (abbr.: $Ir(ppy)_3$). The light emitting layer can be formed by adding a light emitting substance to the host material at a proportion of 0.001 to 50 wt %, preferably, 0.03 to 20 wt %.

When the electron transport layer is used, it is provided between the light emitting layer and the electron injection layer. An appropriate material is a metal complex such as tris(8-quinolinolato)aluminum (abbr.: $Alq_3$), tris(4-methyl-8-quinolinolato)aluminum (abbr.: $Almq_3$), bis(10-hydroxybenzo[h]-quinolinato)beryllium (abbr.: $BeBq_2$), bis(2-methyl-8-quinolinolato)(4-hydroxy-biphenylyl)-aluminum (abbr.: BAlq), bis[2-(2'-hydroxyphenyl)-benzoxazolato]zinc (abbr.: $Zn(BOX)_2$), or bis[2-(2'-hydroxyphenyl)-benzothiazolato]zinc (abbr.: $Zn(BTZ)_2$). Alternatively, a hydrocarbon-based compound such as 9,10-diphenylanthracene or 4,4'-bis(2,2-diphenylethenyl)biphenyl is preferable. Moreover, a triazole derivative such as 3-(4-tert-butylphenyl)-4-(4-ethylphenyl)-5-(4-biphenylyl)-1,2,4-triazole or a phenanthroline derivative such as bathophenanthroline or bathocuproin may also be used.

As an electron injecting material for forming the electron injection layer, there is no particular limitation. Specifically, alkali metal salt or alkaline earth metal salt such as calcium fluoride, lithium fluoride, lithium oxide, or lithium chloride is preferable. Alternatively, a layer in which a donor compound such as lithium is added to a so-called electron transporting material such as tris(8-quinolinolato)aluminum (abbr.: $Alq_3$) or bathocuproin (abbr.: BCP) can be used. The electron injection layer is formed to be in contact with a cathode and by using the electron injection layer, a carrier injection barrier can be lowered and carriers are efficiently injected into the light emitting element; as a result, a drive voltage can be reduced.

Note that, although in this embodiment mode, a structure of a light emitting element in which light emission is obtained only from the light emitting layer is described; a light emitting element may be designed so as to provide light emission from another layer such as an electron transport layer or a hole transport layer. For example, light emission can be obtained from a transport layer as well as from the light emitting layer by adding a dopant which contributes to light emission to an electron transport layer or a hole transport layer. If emission colors of light emitting substances used for the light emitting layer and the transport layer are different, a spectrum with light emissions overlapped with each other can be obtained. If emission colors of the light emitting layer and the transport layer are complementary colors with each other, white light emission can be obtained.

Note that a variety of light emitting elements can be manufactured by varying the kinds of the first electrode 101 and the second electrode 103. When a light transmitting material is used for the first electrode 101, light can be emitted from the first electrode 101 side. When the first electrode 101 has a light blocking (particularly, reflective) property and the second electrode 103 has a light transmitting property, light can be emitted from the second electrode 103 side. Furthermore, when both the first electrode 101 and the second electrode 103 have a light transmitting property, light can be emitted from both the first electrode side and the second electrode side.

Embodiment Mode 3

A light emitting device of the present invention is described in this embodiment mode with reference to FIGS. 2A to 3C. Note that, although this embodiment mode describes an example of manufacturing an active matrix light emitting device, needless to say, the present invention can be applied to a passive matrix light emitting device.

Figure 2A:
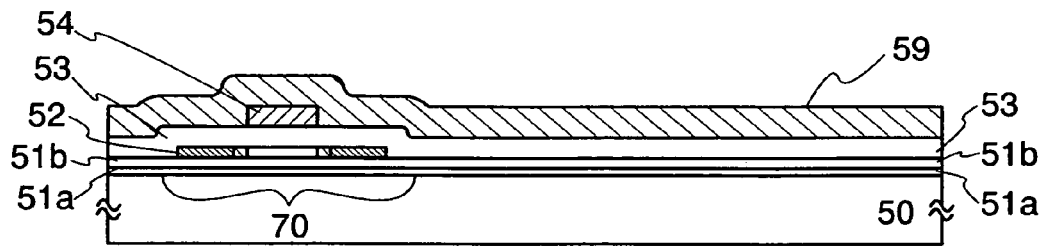
FIGS. 2A to 2E show cross-sectional views of a manufacturing process for an active matrix light emitting device of the present invention.

First, a first base insulating layer 51a and a second base insulating layer 51b are formed over a substrate 50. Then, a semiconductor layer is formed over the second base insulating layer 51b (FIG. 2A).

As a material for the substrate 50, glass, quartz, plastic (such as polyimide, acrylic, polyethylene terephthalate, polycarbonate, polyacrylate, or polyethersulfone), or the like can be used. The substrate may be used after being polished by CMP or the like if necessary. In this embodiment mode, a glass substrate is used.

The first base insulating layer 51a and the second base insulating layer 51b are provided to prevent an element which adversely affects characteristics of the semiconductor film, such as alkali metal or alkaline earth metal in the substrate 50 from diffusing into the semiconductor layer. As a material of the first base insulating layer 51a and the second base insulating layer 51b, silicon oxide, silicon nitride, silicon oxide containing nitrogen, silicon nitride containing oxygen, or the like can be used. In this embodiment mode, silicon nitride is used for the first base insulating layer 51a and silicon oxide is used for the second base insulating layer 51b. The base insulating layer of this embodiment mode has a two-layer structure including the first base insulating layer 51a and the second base insulating layer 51b. However, the base insulating layer may be a single-layer or a multilayer including two or more layers. Note that when an impurity which diffuses from the substrate does not raise a problem, the base insulating layer does not need to be provided.

Next, in this embodiment mode, the semiconductor layer which is subsequently formed is obtained by crystallizing an amorphous silicon film with a laser. An amorphous silicon film is formed over the second base insulating layer 51b to have a thickness of 25 to 100 nm (preferably, 30 to 60 nm). As a forming method, a sputtering method, a low pressure CVD method, a plasma CVD method, or the like can be used. Then, heat treatment is performed at 500° C. for one hour for dehydrogenation.

Then, the amorphous silicon film is crystallized using a laser irradiation apparatus to form a crystalline silicon film. In the laser crystallization of this embodiment mode, an excimer laser is used. An emitted laser beam is processed into a linear beam spot by using an optical system. The crystalline silicon film is formed by irradiating the amorphous silicon film with this linear laser beam and is used as the semiconductor layer. Note that the amorphous silicon film may be used as the semiconductor layer as it is.

As another method for crystallizing the amorphous silicon film, there is a crystallization method conducted only by heat treatment, a method conducted by using a catalytic element which promotes crystallization and performing heat treatment, or the like. As the element which promotes crystallization, nickel, iron, palladium, tin, lead, cobalt, platinum, copper, gold, or the like can be used. The method using such an element can realize crystallization at a lower temperature and in a shorter time than the crystallization method conducted only by heat treatment. Therefore, there is less damage to a glass substrate and the like. In the case of using the crystallization method conducted only by heat treatment, a quartz substrate which is resistant to heat is preferably used as the substrate 50.

Next, if necessary, a slight amount of impurity for controlling a threshold value is added to the semiconductor layer, that is, so-called channel doping is performed. In order to obtain a required threshold value, an impurity imparting n-type or p-type conductivity (such as phosphorus or boron) is added by an ion-doping method or the like.

Subsequently, the semiconductor layer is processed into a desired shape to obtain an island-shaped semiconductor layer 52 as shown in FIG. 2A. The semiconductor layer is shaped as follows. A photoresist is applied to the semiconductor layer to be exposed to light and a predetermined mask shape is formed, and the photoresist is baked; then, the semiconductor layer is etched with the mask so that the island-shaped semiconductor layer 52 can be formed.

Subsequently, a gate insulating layer 53 is formed to cover the semiconductor layer 52. The gate insulating layer 53 is formed by an insulating layer containing silicon to have a thickness of 40 to 150 nm by a plasma CVD method or a sputtering method. In this embodiment mode, the gate insulating layer 53 is formed using silicon oxide.

Then, a gate electrode 54 is formed over the gate insulating layer 53. The gate electrode 54 may be formed of an element selected from tantalum, tungsten, titanium, molybdenum, aluminum, copper, chromium, and niobium, or an alloy material or compound material containing the foregoing element as its main component. Alternatively, a semiconductor film which is typified by a polycrystalline silicon film doped with an impurity element such as phosphorus may be used. Further alternatively, an Ag—Pd—Cu alloy may be used.

In this embodiment mode, the gate electrode 54 is a single-layer. However, it may have a stacked-layer structure including two or more layers such as a two-layer structure including a lower layer of tungsten and an upper layer of molybdenum. When the gate electrode is formed to have a stacked-layer structure, the foregoing material may be used. A combination of the materials may be selected appropriately. The gate electrode 54 is processed by forming a mask using a photo resist and etching with the mask formed of the photoresist.

Next, an impurity is added to the semiconductor layer 52 at a high concentration using the gate electrode 54 as a mask.

Accordingly, a thin film transistor 70 including the semiconductor layer 52, the gate insulating layer 53, and the gate electrode 54 is formed.

Note that a manufacturing process for the thin film transistor is not limited in particular and may be changed appropriately so that a transistor having a desired structure can be manufactured.

In this embodiment mode, a top-gate thin film transistor using the crystalline silicon film which is crystallized by laser crystallization is used. However, a bottom-gate thin film transistor using an amorphous semiconductor film can be used in a pixel portion. In addition, silicon germanium as well as silicon can be used as the amorphous semiconductor. In the case of using silicon germanium, the concentration of germanium is preferably about 0.01 to 4.5 atomic %.

Subsequently, an insulating film (hydride film) 59 is formed of silicon nitride to cover the gate electrode 54 and the gate insulating layer 53. After forming the insulating film (hydride film) 59, the impurity element is activated and the semiconductor layer 52 is hydrogenated by performing heat treatment at 480° C. for about one hour.

Figure 2B:
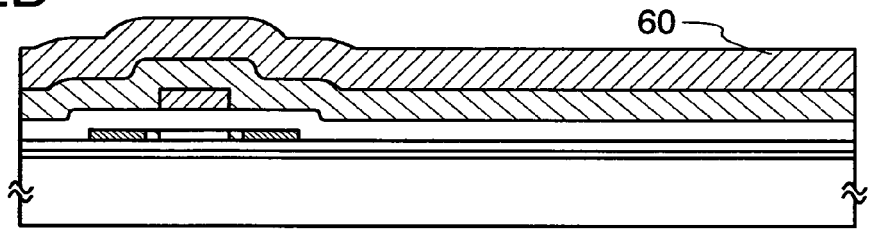

Next, a first interlayer insulating layer 60 is formed to cover the insulating film (hydride film) 59. As a material for forming the first interlayer insulating layer 60, silicon oxide, acrylic, polyimide, siloxane, a low-k material, or the like is preferably used. In this embodiment mode, a silicon oxide film is formed as the first interlayer insulating layer (FIG. 2B).

Figure 2C:
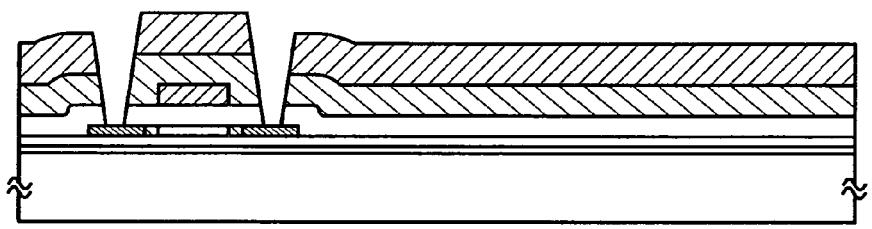

Next, a contact hole that reaches the semiconductor layer 52 is formed. The contact holes can be formed by etching to expose the semiconductor layer 52 using a resist mask. The contact hole can be formed by either a wet etching or dry etching. Note that etching may be performed once or a plurality of times. When etching is performed a plurality of times, both wet etching and dry etching may be performed (FIG. 2C).

Figure 2D:
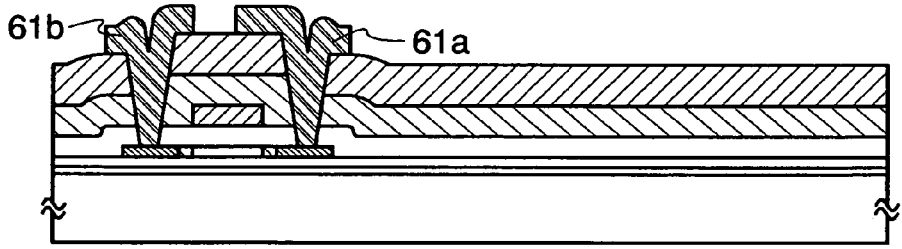

Then, a conductive layer is formed to cover the contact hole and the first interlayer insulating layer 60. The conductive layer is processed into a desired shape, thereby forming a connection portion 61a, a wire 61b, and the like. This wire may be a single-layer of aluminum, copper, an alloy of aluminum, carbon, and nickel, an alloy of aluminum, carbon, and molybdenum, or the like. The wire may have a stacked-layer structure in which molybdenum, aluminum, and molybdenum are sequentially formed over the substrate, a stacked-layer structure in which titanium, aluminum, and titanium are sequentially formed over the substrate, a stacked-layer structure in which titanium, titanium nitride, aluminum, and titanium are sequentially formed over the substrate, or the like (FIG. 2D).

Figure 2E:
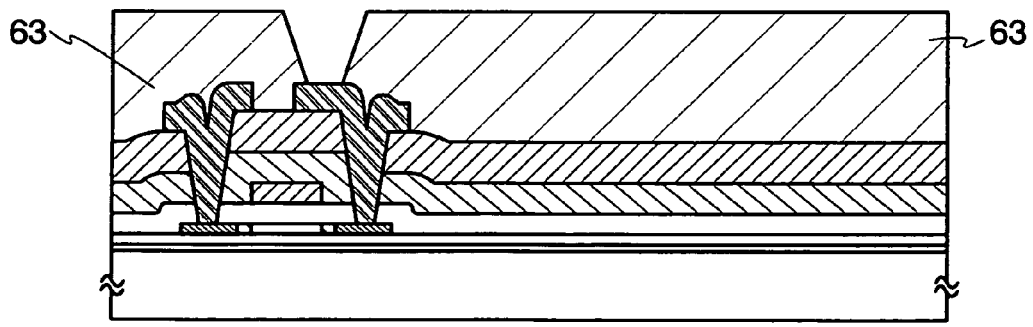

Subsequently, a second interlayer insulating layer 63 is formed to cover the connection portion 61a, the wire 61b, and the first interlayer insulating layer 60. As a material for the second interlayer insulating layer 63, a self-planarizing material such as acrylic, polyimide, or siloxane is preferably used to be applied. In this embodiment mode, siloxane is used for the second interlayer insulating layer 63 (FIG. 2E).

Next, an insulating layer may be formed of silicon nitride or the like over the second interlayer insulating layer 63. The formation of the insulating layer can prevent the second interlayer insulating layer 63 from being etched more than necessary while etching a pixel electrode to be formed later. Note that the insulating layer is not necessarily formed when the ratio of etching rate between the pixel electrode and the second interlayer insulating layer 63 is high. Subsequently, a contact hole which penetrates the second interlayer insulating layer 63 and reaches the connection portion 61a is formed.

Figure 3A:
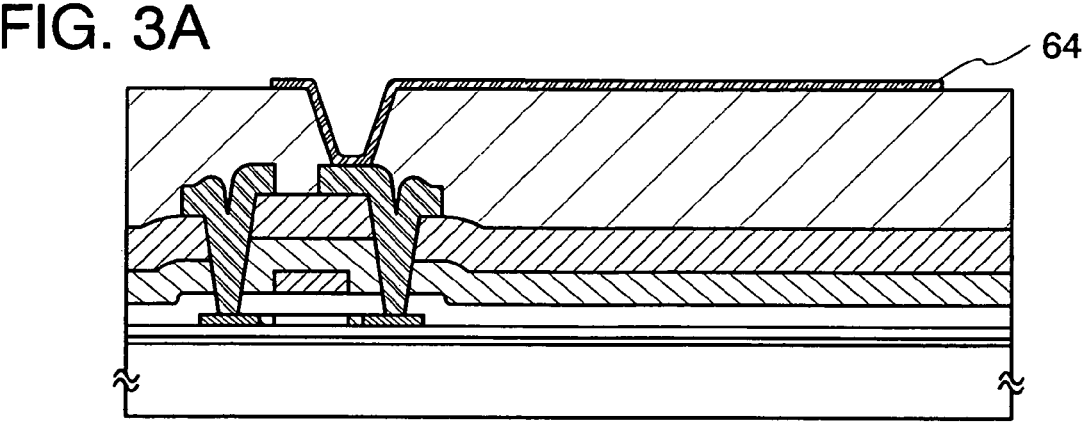
FIGS. 3A to 3C show cross-sectional views of a manufacturing process for an active matrix light emitting device of the present invention.

Then, a conductive layer is formed to cover the contact hole and the second interlayer insulating layer 63 (or the insulating layer). Subsequently, the conductive layer is processed to form a first electrode 64 in a thin-film light emitting element. Here, the first electrode 64 is electrically in contact with the connection portion 61a (FIG. 3A).

The first electrode 64 can be formed by a conductive film using conductive metal such as aluminum (Al), silver (Ag), gold (Au), platinum (Pt), nickel (Ni), tungsten (W), chromium (Cr), molybdenum (Mo), iron (Fe), cobalt (Co), copper (Cu), palladium (Pd), lithium (Li), cesium (Cs), magnesium (Mg), calcium (Ca), strontium (Sr), or titanium (Ti); an alloy thereof such as an alloy of aluminum and silicon (Al—Si), an alloy of aluminum and titanium (Al—Ti), or an alloy of aluminum, silicon, and copper (Al—Si—Cu); nitride such as titanium nitride (TiN); a metal compound such as indium tin oxide (ITO), ITO containing silicon oxide (hereinafter referred to as ITSO), or indium zinc oxide (IZO) in which indium oxide is mixed with zinc oxide (ZnO) at 2 to 20 wt %; or the like.

In addition, an electrode through which light emission is extracted may be formed using a transparent conductive film and an extremely thin film of metal such as Al or Ag, as well as a metal compound such as ITO, ITSO, or IZO is used. When light emission is extracted through a second electrode, the first electrode can be formed of a highly reflective material (such as Al or Ag). In this embodiment mode, ITSO is used for the first electrode 64 (FIG. 3A).

Figure 3B:
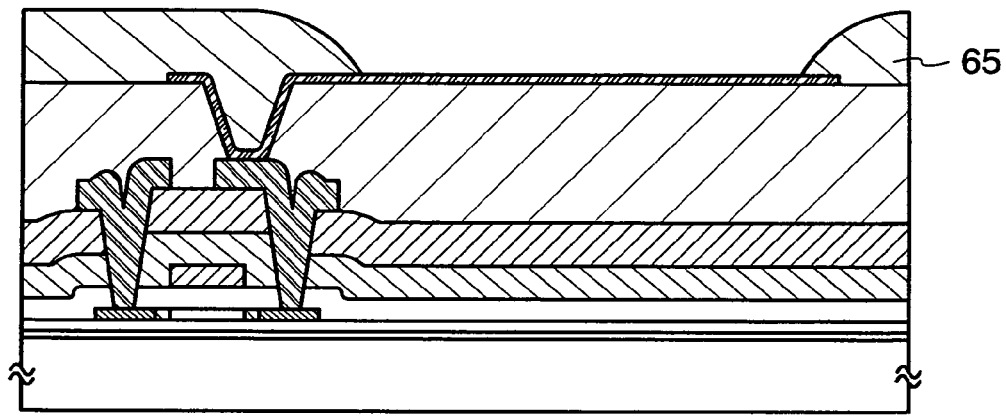

Next, an insulating layer is formed of an organic material or an inorganic material to cover the second interlayer insulating layer 63 (or the insulating layer) and the first electrode 64. Subsequently, the insulating layer is processed so as to partially expose the first electrode 64, thereby forming a partition wall 65. The partition wall 65 is preferably formed of a photosensitive organic material (such as acrylic or polyimide). Note that the partition wall 65 may be formed of a non-photosensitive organic material or inorganic material. The partition wall 65 may be blacked by dispersing a black colorant or dye such as titanium black or carbon nitride in the material of the partition wall 65 using a dispersant or the like, whereby the black partition wall 65 is used as a black matrix. An end surface of the partition wall 65 facing the first electrode preferably has curvature and a tapered shape in which the curvature changes continuously (FIG. 3B).

Figure 3C:
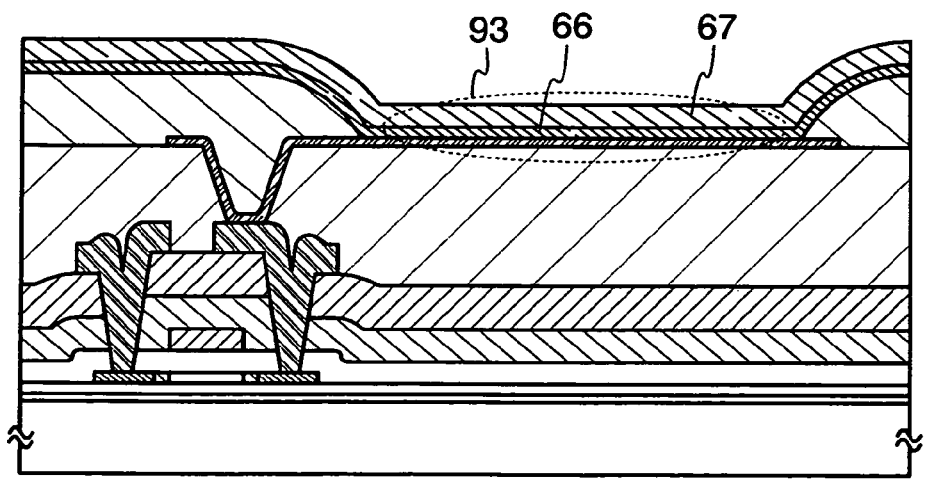

Next, an organic compound containing layer 66 is formed. Then, the second electrode 67 is formed to cover the organic compound containing layer 66. Accordingly, a light emitting element 93 where the organic compound containing layer 66 is interposed between the first electrode 64 and the second electrode 67 can be manufactured. Light emission can be obtained by applying higher voltage to the first electrode 64 than to the second electrode 67. The second electrode 67 can be formed of an electrode material similar to that of the first electrode 64. In this embodiment mode, aluminum is used for the second electrode 67 (FIG. 3C).

The organic compound containing layer 66 can be formed using either a low molecular material or a high molecular material. The organic compound containing layer 66 in this embodiment mode contains the stilbene derivative described in Embodiment Mode 1. Note that a material for the organic compound containing layer 66 is not limited to a material containing only an organic compound material, and it may partially contain an inorganic compound material. The organic compound containing layer 66 can be formed by either a wet method or a dry method such as an evaporation method, an ink-jet method, a spin coating method, or a dip coating method. In addition, the organic compound containing layer 66 may be formed by appropriately combining functional layers having respective functions, such as a hole injection layer, a hole transport layer, a hole blocking layer, a light emitting layer, an electron transport layer, and an electron injection layer. The functional layers may include a layer having two or more functions at the same time. In this embodiment mode, a stacked-layer structure including a hole injection layer, a hole transport layer, a light emitting layer, an electron transport layer, and an electron injection layer is employed. In a light emitting layer in the light emitting device in this embodiment mode, the stilbene derivative described in Embodiment Mode 1 is used. There is no particular limitation on other functional layers in the organic compound containing layer 66, and materials thereof has been described in Embodiment Mode 2; therefore, a repeated description is omitted.

Subsequently, a silicon oxide film containing nitrogen is formed as a passivation film by a plasma CVD method. In the case of using the silicon oxide film containing nitrogen, a silicon oxynitride film may be formed by a plasma CVD method using $SiH_4$, $N_2O$, and $NH_3$; using $SiH_4$ and $N_2O$; or using a gas in which $SiH_4$ and $N_2O$ are diluted with Ar.

A silicon oxynitride hydride film may be formed of $SiH_4$, $N_2O$, and $H_2$ may be used as the passivation film. Needless to say, a structure of the passivation film is not limited to a single-layer structure. The passivation film may have a single-layer structure or a stacked-layer structure including another insulating layer containing silicon. In addition, a multilayer film including a carbon nitride film and a silicon nitride film, a multilayer film including styrene polymer, a silicon nitride film, or a diamond-like carbon film may be used in stead of the silicon oxide film containing nitrogen.

Then, a display portion is sealed to protect the light emitting element 93 from a substance which promotes deterioration, such as moisture. In the case of using a counter substrate for sealing, the counter substrate is attached using an insulating sealant so that an external connection portion is exposed. A space between the counter substrate and an element substrate may be filled with a dry inert gas such as nitrogen, or the counter substrate may be attached using a sealant applied entirely over the pixel portion. It is preferable to use an ultraviolet curing resin or the like as the sealant. The sealant may be mixed with a drying agent or particles for keeping a gap between the substrates constant. Then, a flexible wiring board is attached to the external connection portion, thereby completing a light emitting device.

An example of a structure of the light emitting device manufactured as described above is explained with reference to FIGS. 4A and 4B. Note that portions having similar functions are denoted by the same reference numeral even if they have different shapes, and explanation thereof may be omitted. In this embodiment mode, the thin film transistor 70 having an LDD structure is connected to the light emitting element 93 through the connection portion 61a.

Figure 4A:
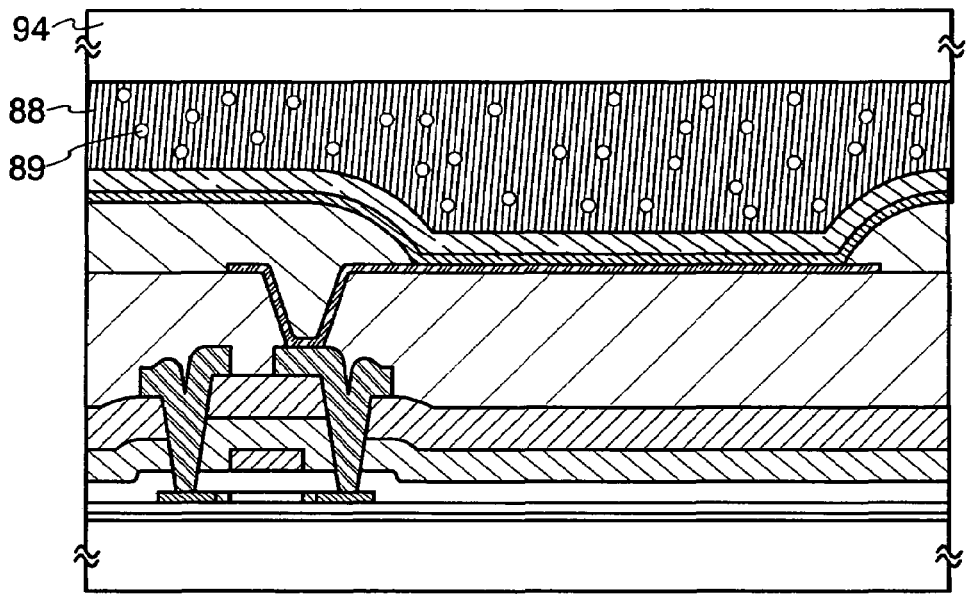
FIGS. 4A and 4B show cross-sectional views of an active matrix light emitting device of the present invention.

FIG. 4A shows a structure in which the first electrode 64 is formed of a light transmitting conductive film and light emitted from the organic compound containing layer 66 is extracted to the substrate 50 side. Note that 94 denotes the counter substrate. The counter substrate is fixed to the substrate 50 with a sealant or the like after the light emitting element 93 is formed. A space between the counter substrate 94 and the element can be filled with a light transmitting resin 88 or the like, and sealing can be performed; whereby deterioration of the light emitting element 93 due to moisture can be prevented. The light transmitting resin 88 is preferably hygroscopic. When a highly light transmitting drying agent 89 is dispersed in the resin 88, an influence of the moisture can be further reduced, which is more preferable.

Figure 4B:
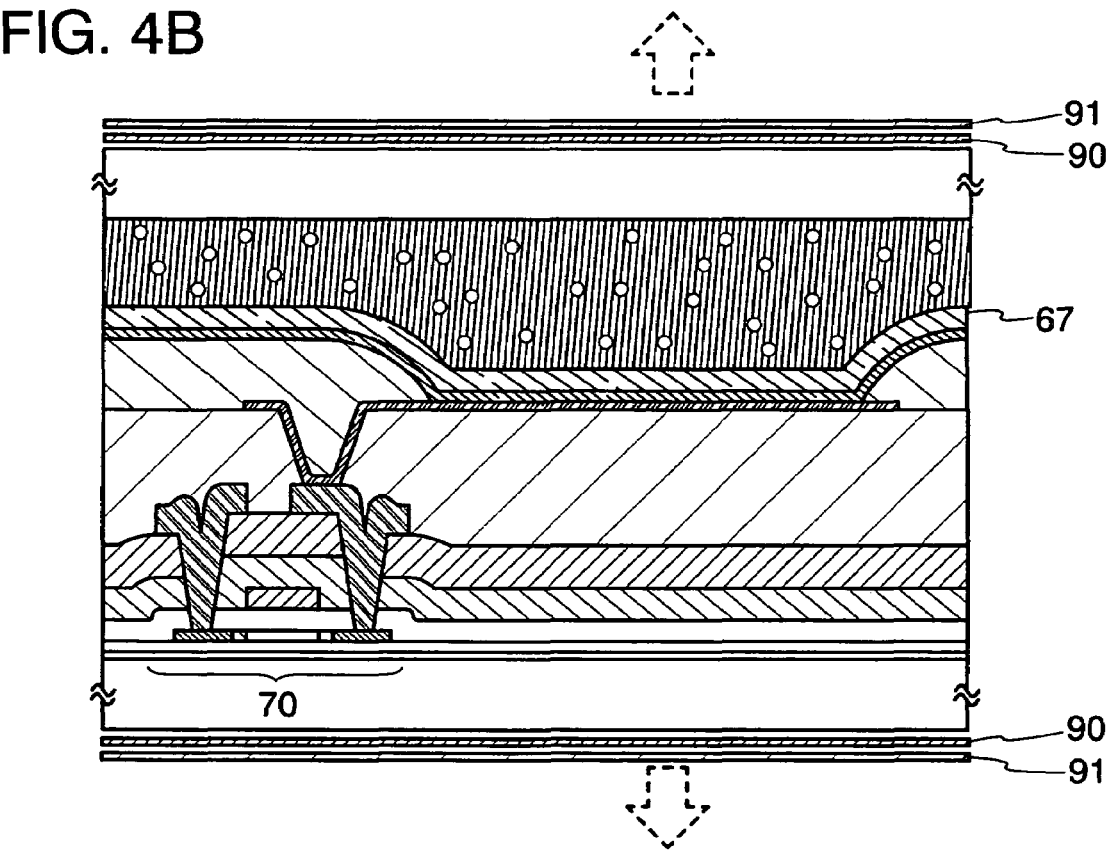

FIG. 4B shows a structure in which each of the first electrode 64 and the second electrode 67 is formed of a light transmitting conductive film and light can be extracted to both the substrate 50 side and the counter substrate 94 side. In this structure, a screen can be prevented from being transparent by providing a polarizing plate 90 to outside of each of the substrate 50 and the counter substrate 94; thus, visibility is improved. A protective film 91 is preferably provided outside the polarizing plate 90.

Although a top gate thin film transistor is used in this embodiment mode, a thin film transistor having another structure such as a bottom gate thin film transistor may be used for manufacturing a light emitting device.

Note that either an analog video signal or a digital video signal may be used for a light emitting device of the present invention having a display function. In the case of using a digital video signal, there are cases where the video signal uses voltage and the video signal uses current. As a video signal which is inputted to a pixel when a light emitting element emits light, there are a constant voltage video signal and a constant current video signal. As the constant voltage video signal, there are a signal in which voltage applied to a light emitting element is constant and a signal in which current flowing to a light emitting element is constant. As the constant current video signal, there are a signal in which voltage applied to a light emitting element is constant and a signal in which current flowing to a light emitting element is constant. Drive with the signal in which voltage applied to a light emitting element is constant is constant voltage drive, and that with the signal in which current flowing to a light emitting element is constant is constant current drive. By constant current drive, constant current flows regardless of a change in resistance of the light emitting element. For a light emitting device of the present invention and a driving method thereof, any of the foregoing driving methods may be employed.

In a light emitting device of the present invention including the stilbene derivative described in Embodiment Mode 1 in the organic compound containing layer 66, an energy gap of the stilbene derivative is large and excitation energy does not move to a host material from a light emitting substance. Thus, a light emitting device of the present invention can have reduced power consumption and an improved display quality. In addition, in a light emitting device of the present invention, since the stilbene derivative has an electron transporting property, a light emitting element with high emission efficiency and color purity is easily designed, whereby a light emitting device of the present invention can have reduced power consumption and an improved display quality. Further in addition, in a light emitting device of the present invention, since the stilbene derivative is a material having a large energy gap and an electron transporting property, excitation energy does not move to a host material from a light emitting substance; whereby a light emitting element is easily designed. Thus, a light emitting device of the present invention can have reduced power consumption and an improved display quality.

This embodiment mode can be combined with an appropriate structure in Embodiment Mode 1 or 2.

Embodiment Mode 4

Figure 5A:
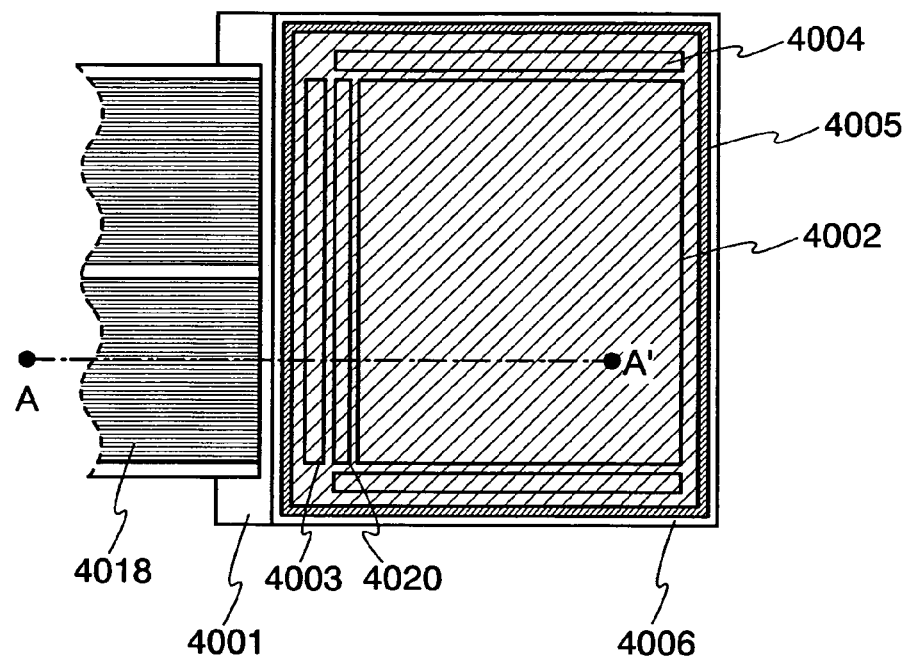
FIGS. 5A and 5B show a top view and cross-sectional view of a light emitting device of the present invention.
Figure 5B:
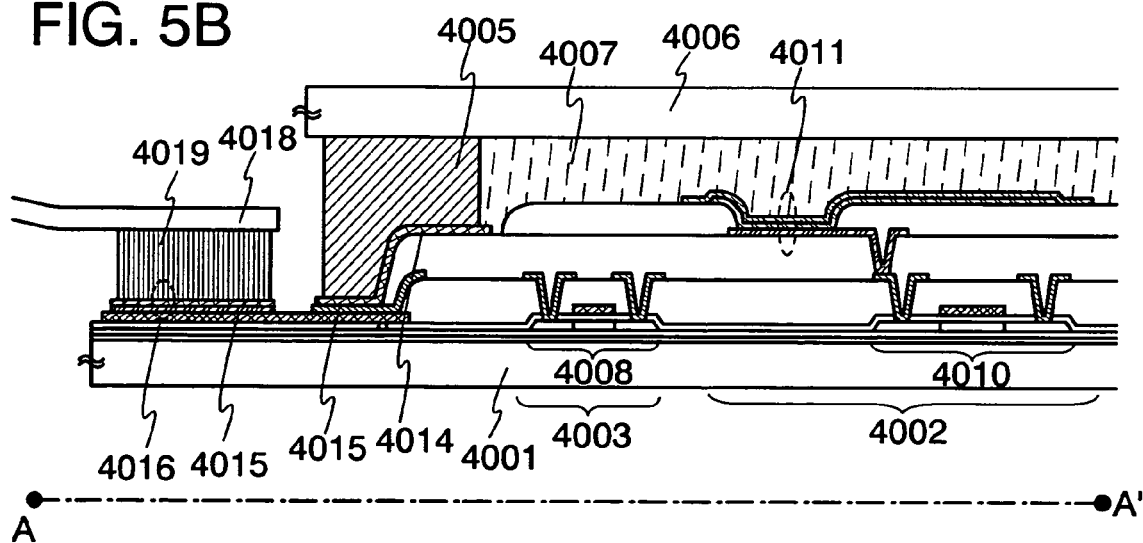

An appearance of a panel which is a light emitting device of the present invention is described in this embodiment mode with reference to FIGS. 5A and 5B. FIG. 5A is a top view of a panel in which a transistor and a light emitting element 4011 formed over a substrate 4001 are sealed with a sealant 4005 formed between the substrate 4001 and a counter substrate 4006. FIG. 5B corresponds to a cross-sectional view of FIG. 5A. The light emitting element mounted on this panel has a structure similar to that described in Embodiment Mode 2.

The sealant 4005 is provided to surround a pixel portion 4002, a signal line driver circuit 4003, and a scan line driver circuit 4004 which are provided over the substrate 4001. The counter substrate 4006 is provided over the pixel portion 4002, the signal line driver circuit 4003, and the scan line driver circuit 4004. Thus, the pixel portion 4002, the signal line driver circuit 4003, a driver circuit 4020, and the scan line driver circuit 4004 are sealed with the substrate 4001, the sealant 4005, and the counter substrate 4006 as well as a filler 4007.

The pixel portion 4002, the signal line driver circuit 4003, and the scan line driver circuit 4004 which are provided over the substrate 4001 include a plurality of thin film transistors. FIG. 5B shows a thin film transistor 4008 included in the signal line driver circuit 4003 and a thin film transistor 4010 included in the pixel portion 4002.

The light emitting element 4011 is electrically connected to the thin film transistor 4010.

A lead wire 4014 corresponds to a wire for supplying signals or power voltage to the pixel portion 4002, the signal line driver circuit 4003, and the scan line driver circuit 4004. The lead wire 4014 is connected to a connection terminal 4016 through a lead wire 4015. The connection terminal 4016 is electrically connected to a terminal included in a flexible printed circuit 4018 through an anisotropic conductive film 4019.

Note that an ultraviolet curing resin or a thermosetting resin as well as an inert gas such as nitrogen or argon can be used as the filler 4007. Polyvinyl chloride, acrylic, polyimide, an epoxy resin, a silicon resin, polyvinyl butyral, or ethylene vinylene acetate can be used.

Note that a light emitting device of the present invention includes, in its category, a panel provided with a pixel portion having a light emitting element and a module in which an IC is mounted on the panel.

The signal line driver circuit 4003, the scan line driver circuit 4004, and the IC, which are signal processing circuits as described above are control circuits of a light emitting element, and a light emitting device and an electronic appliance having these control circuits can display various images on the panel by the control circuits controlling lighting and non-lighting or luminance. Note that a signal processing circuit which is formed over an external circuit board connected through the flexible printed circuit 4018 is also a control circuit.

A light emitting device of the present invention as described above is a light emitting device having a pixel portion with reduced power consumption and an improved display quality because the pixel portion includes the light emitting element described in Embodiment Mode 2 which includes the stilbene derivative described in Embodiment Mode 1 in an organic compound containing layer. In addition, a light emitting device of the present invention as described above is a light emitting device with reduced power consumption and an improved display quality because the light emitting device includes the light emitting element described in Embodiment Mode 2 as a light emitting element included in the pixel portion which includes the stilbene derivative described in Embodiment Mode 1 in an organic compound containing layer.

This embodiment mode can be combined with a structure in Embodiment Modes 1 to 3 arbitrarily.

Embodiment Mode 5

A pixel circuit and a protective circuit which are included in the panel or module described in Embodiment Mode 4, and operation thereof are described in this embodiment mode. Note that the cross-sectional views shown in FIGS. 2A to 3C correspond to schematic cross-sectional views of a driver TFT 1403 and a light emitting element 1405.

Figure 6A:
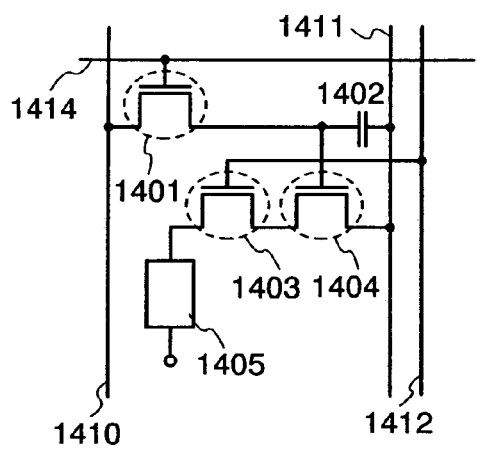
FIGS. 6A to 6F show examples of a pixel circuit in a light emitting device of the present invention.

A pixel shown in FIG. 6A has a structure in which a signal line 1410 and power source lines 1411 and 1412 are arranged in a column direction and a scan line 1414 is arranged in a row direction. In addition, the pixel includes a switching TFT 1401, the driver TFT 1403, a current control TFT 1404, a capacitor 1402, and the light emitting element 1405.

Figure 6B:
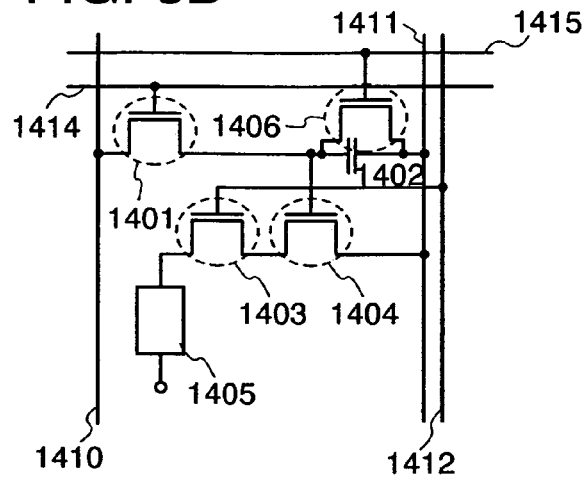
Figure 6C:
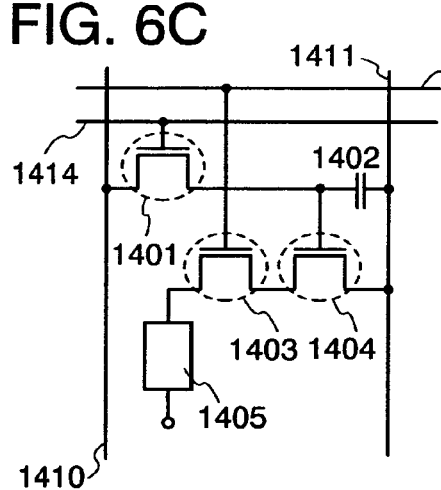
Figure 6D:
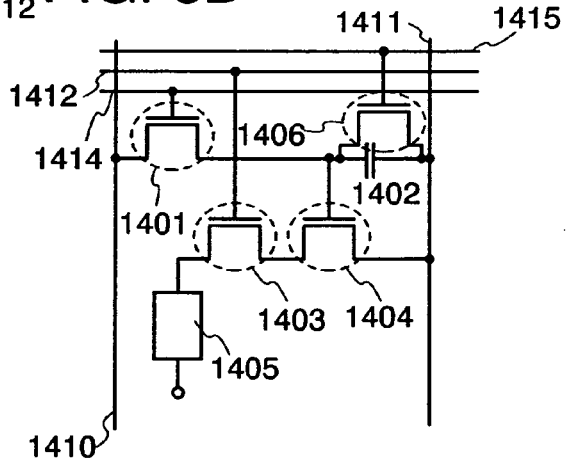

A pixel shown in FIG. 6C has the same structure as that of the pixel shown in FIG. 6A, except that a gate electrode of the driver TFT 1403 is connected to the power source line 1412 arranged in a row direction. In other words, equivalent circuit diagrams of both pixels shown in FIGS. 6A and 6C are the same. Note that each of the power source line 1412 arranged in a row direction (FIG. 6A) and the power source line 1412 arranged in a column direction (FIG. 6C) is formed using a conductive layer in different layers. Here, the pixels are separately shown in FIGS. 6A and 6C to show that wires each connected to the gate electrode of the driver TFT 1403 are formed in different layers.

In each of the pixels shown in FIGS. 6A and 6C, the driver TFT 1403 is connected in series to the current control TFT 1404 in the pixel. A channel length L (1403) of the driver TFT 1403 and a channel width W (1403) of the driver TFT 1403 and a channel length L (1404) of the current control TFT 1404 and a channel width W (1404) of the current control TFT 1404 are preferably set so as to satisfy L (1403)/W (1403):L (1404)/W (1404)=5 to 6000:1.

Note that the driver TFT 1403 operates in a saturation region and has a role of controlling a current value flowing to the light emitting element 1405. The current control TFT 1404 operates in a linear region and has a role of controlling the supply of current to the light emitting element 1405. It is preferable from the viewpoint of the manufacturing process that both TFTs have the same conductivity type. In this embodiment mode, both TFTs are formed as n-channel TFTs. Further, the driver TFT 1403 may be a depletion mode TFT as well as an enhancement mode TFT. In a light emitting device of the present invention having the foregoing structure, the current control TFT 1404 operates in a linear region, so that slight variation in Vgs (gate-source voltage) of the current control TFT 1404 does not affect the current value of the light emitting element 1405. In other words, the current value of the light emitting element 1405 can be determined depending on the driver TFT 1403 which operates in the saturation region. According to the foregoing structure, luminance variation of the light emitting element, which is caused by characteristics variation of the TFTs, can be suppressed, and a light emitting device with a high image quality can be provided.

In each of pixels shown in FIGS. 6A to 6D, the switching TFT 1401 controls the input of a video signal to the pixel. When the switching TFT 1401 turns on, the video signal is inputted to the pixel. Then, voltage of that video signal is held at the capacitor 1402. Note that, although each of FIGS. 6A and 6C shows a structure provided with the capacitor 1402, the present invention is not limited thereto. When a capacitance value of a gate capacitor or the like is sufficient for holding a video signal, the capacitor 1402 is not necessarily provided.

The pixel shown in FIG. 6B has the same structure as that of the pixel shown in FIG. 6A, except that a TFT 1406 and a scan line 1415 are added. In the same manner, the pixel shown in FIG. 6D has the same structure as that of the pixel shown in FIG. 6C, except that the TFT 1406 and the scan line 1415 are added.

The TFT 1406 is controlled to be turned on or off by the scan line 1415 that is newly provided. When the TFT 1406 turns on, an electric charge held at the capacitor 1402 is discharged, and the current control TFT 1404 turns off. In other words, it is possible to forcibly make a state in which current does not flow to the light emitting element 1405 by providing the TFT 1406. Therefore, the TFT 1406 can be referred to as an erase TFT. Accordingly, in the structures of FIGS. 6B and 6D, a lighting period can be started simultaneously with or immediately after a start of a write period without waiting for writing of signals in all pixels. Therefore, a duty ratio can be increased.

Figure 6E:
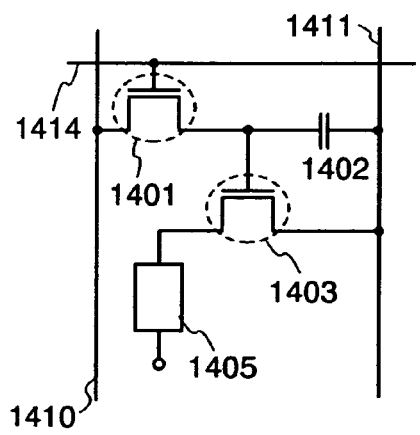
Figure 6F:
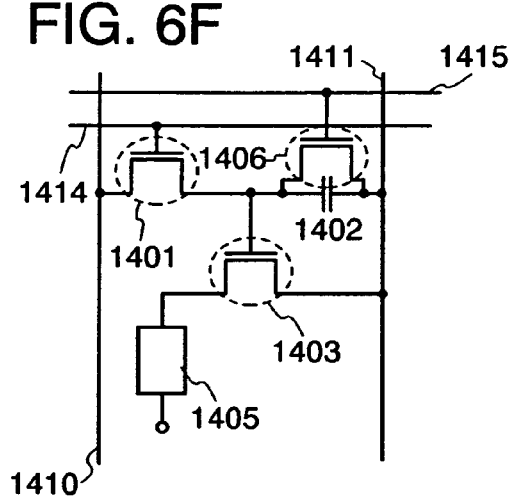

A pixel shown in FIG. 6E has a structure in which the signal line 1410 and the power source line 1411 are arranged in a column direction, and the scan line 1414 is arranged in a row direction. In addition, the pixel includes the switching TFT 1401, the driver TFT 1403, the capacitor 1402, and the light emitting element 1405. A pixel shown in FIG. 6F has the same structure as that of the pixel shown in FIG. 6E, except that the TFT 1406 and the scan line 1415 are added. Note that a duty ratio can be increased also in the structure of FIG. 6F by providing the TFT 1406.

As described above, various pixel circuits can be employed in the present invention. In particular, in the case of forming a thin film transistor with an amorphous semiconductor film, a size of a semiconductor film in the driver TFT 1403 is preferably large. Therefore, the foregoing pixel circuit is preferably a top emission type which emits light from an organic compound containing layer through a sealing substrate side.

Such an active matrix light emitting device is considered to be advantageous in that it can be driven at low voltage when a pixel density is increased, because each pixel is provided with a TFT.

Although an active matrix light emitting device in which each pixel is provided with a TFT is described in this embodiment mode, the present invention can be applied also to a passive matrix light emitting device. Since a TFT is not provided for every pixel in a passive matrix light emitting device, a high aperture ratio can be obtained. In the case of a light emitting device which emits light to both sides of an organic compound containing layer, an aperture ratio can be increased by using the passive matrix light emitting device.

Subsequently, a case of providing a diode as a protective circuit to a scan line and a signal line is described using an equivalent circuit shown in FIG. 6E.

Figure 7:
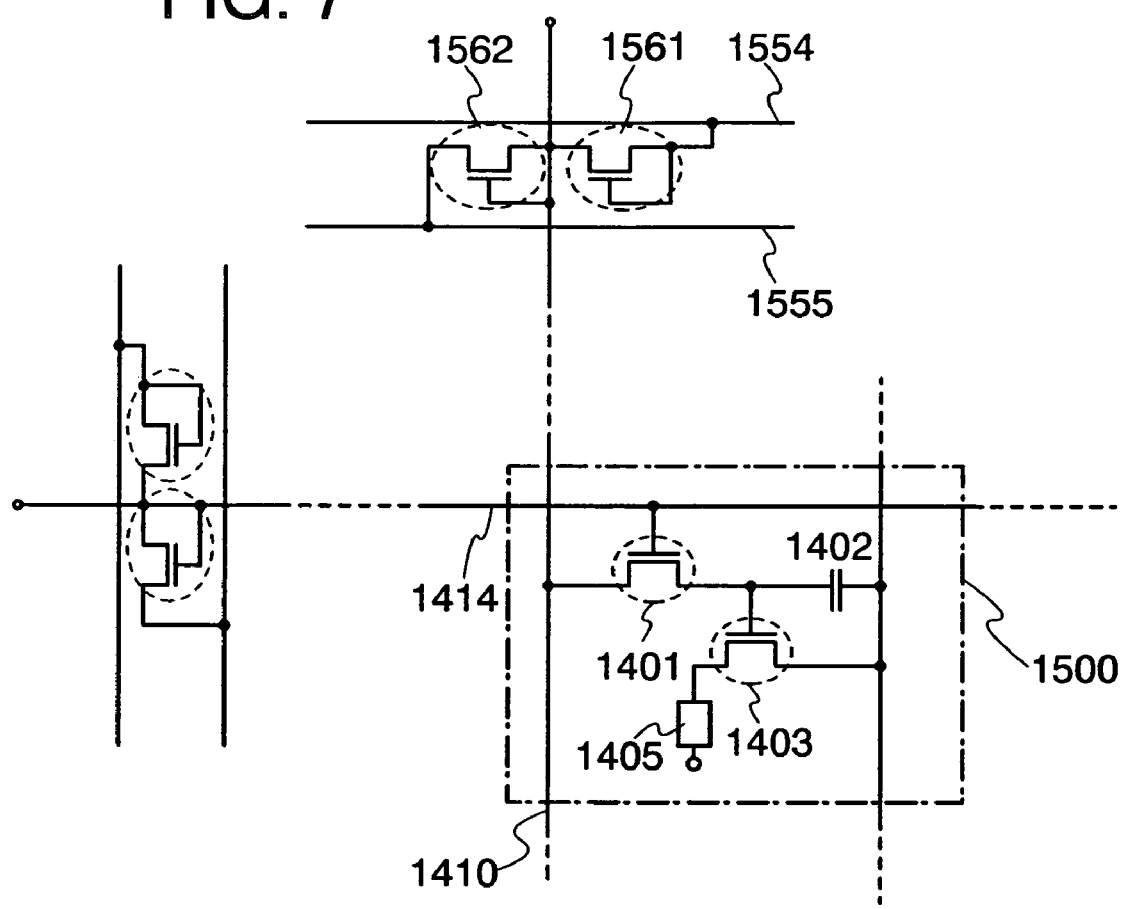
FIG. 7 shows an example of a protective circuit in a light emitting device of the present invention.

In FIG. 7, a pixel portion 1500 is provided with the switching TFT 1401, the driver TFT 1403, the capacitor 1402, and the light emitting element 1405. The signal line 1410 is provided with diodes 1561 and 1562. Each of the diodes 1561 and 1562 is manufactured by the method in the foregoing embodiment mode as is the case with the switching TFT 1401 or the driver TFT 1403. Therefore, each diode includes a gate electrode, a semiconductor layer, a source electrode and a drain electrode, and the like. Each of the diodes 1561 and 1562 is operated as a diode by connecting the gate electrode to the source or drain electrode.

Common potential lines 1554 and 1555 connected to the diodes are formed in the same layer as the gate electrode. Therefore, a contact hole needs to be formed in a gate insulating layer to connect each of the common potential lines to the source or drain electrode of the diode.

A diode provided for the scan line 1414 also has a similar structure.

According to the present invention as described above, a protective diode to be provided at an input stage can be formed at the same time as the TFT. Note that the position where the protective diode is formed is not limited thereto. The protective diode can be provided between a driver circuit and a pixel.

This embodiment mode can be combined with structure in Embodiment Modes 1 to 4 arbitrarily.

By providing the foregoing protective circuit, reliability of a light emitting device of the present invention can be increased.

Embodiment Mode 6

Figure 8A:
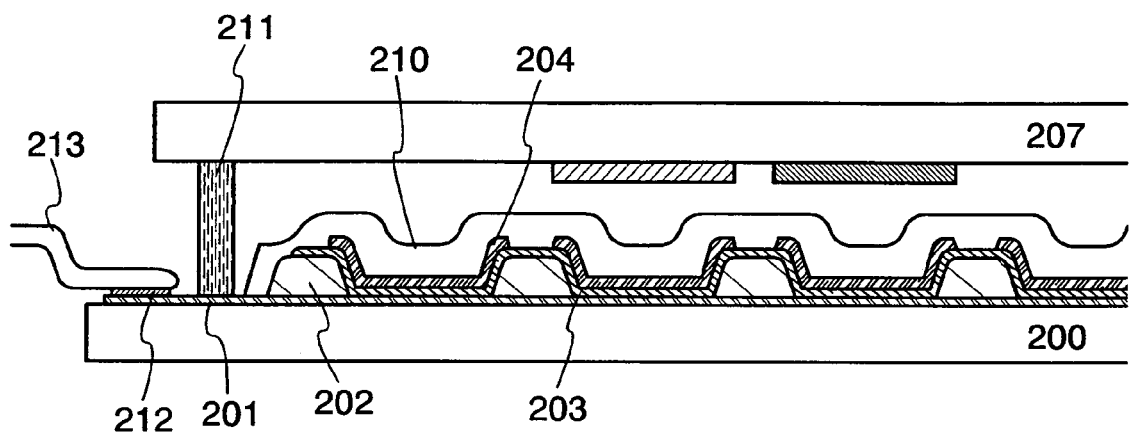
FIGS. 8A and 8B show a top view and a cross-sectional view of a passive matrix light emitting device of the present invention.

FIG. 8A shows an example of a structure of a light emitting device of the present invention. FIG. 8A shows a partial cross-sectional view of a pixel portion in a passive matrix light emitting device having a forward tapered structure. A light emitting device of the present invention shown in FIG. 8A includes a substrate 200, a first electrode 201 of a light emitting element, a partition wall 202, an organic compound containing layer 203, a second electrode 204 of the light emitting element, and a counter substrate 207.

A portion serving as a pixel corresponds to a portion where the organic compound containing layer 203 is interposed between the first electrode 201 and the second electrode 204. The first electrodes 201 and the second electrodes 204 are formed in stripes to be perpendicular to each other, and the portion serving as a pixel is formed at the intersection. The partition wall 202 is formed parallel to the second electrode 204, and the portion serving as a pixel is insulated by the partition wall 202 from another portion serving as a pixel having the same first electrode 201.

In this embodiment mode, Embodiment Mode 2 may be referred to for specific materials and structures of a light emitting element including the first electrode 201, the second electrode 204, and the organic compound containing layer 203.

In addition, the substrate 200, the partition wall 202, and the counter substrate 207 in FIG. 8A correspond to the substrate 50, the partition wall 65, and the counter substrate 94 in Embodiment Mode 3, respectively. Since structures, materials, and effects thereof are similar to those in Embodiment Mode 3, repetitive explanation is omitted. Refer to the description in Embodiment Mode 3.

In the light emitting device, a protective film 210 is formed to prevent the entry of moisture or the like, and the counter substrate 207 formed of glass, quartz, a ceramic material such as alumina, a synthetic material, or the like is firmly attached with a sealing adhesive 211. An external input terminal portion is connected to an external circuit using a flexible printed wiring board 213 through an anisotropic conductive film 212. The protective film 210 may be formed using silicon nitride or a stacked-layer body including carbon nitride and silicon nitride for reducing stress and improving a gas barrier property.

Figure 8B:
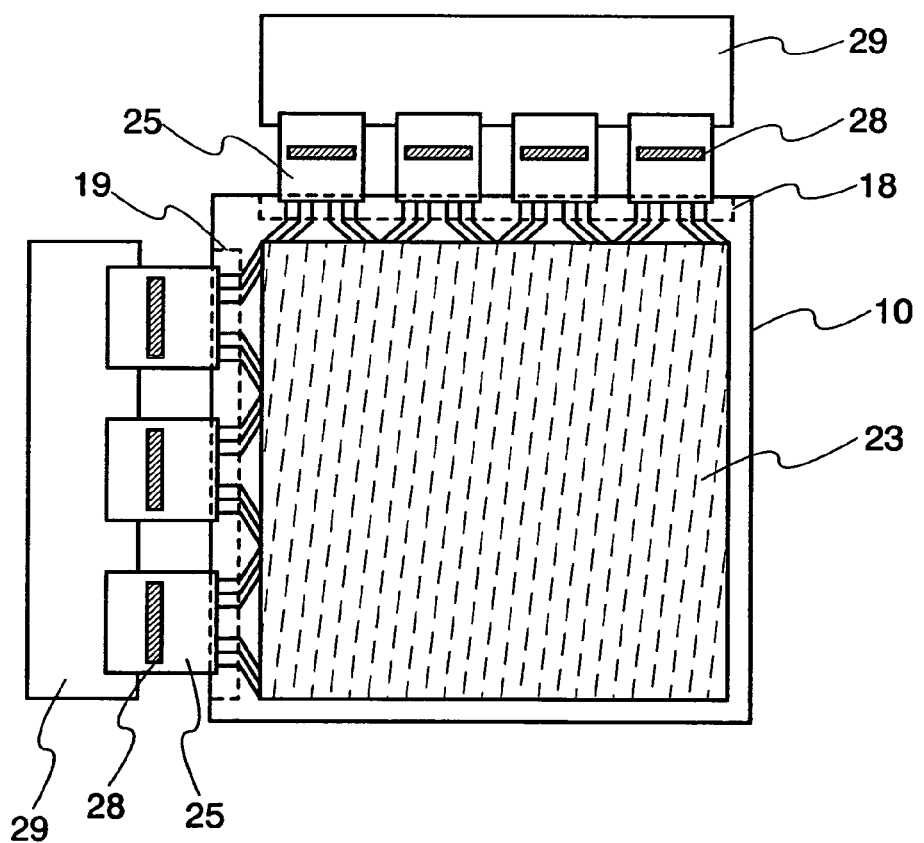

FIG. 8B shows a state of a module which is formed by connecting an external circuit and a panel 10. In the module, flexible printed wiring boards 25 are firmly attached to external input terminal portions 18 and 19, and are electrically connected to external circuit boards 29 provided with power source circuits and signal processing circuits. A driver IC 28 which is one of external circuits may be mounted by either a COG method or a TAB method. FIG. 8B shows a state in which the driver IC 28 which is one of external circuits is mounted by a COG method. The signal processing circuits formed over the external circuit boards and the driver ICs 28 are control circuits of the light emitting element, and a light emitting device and an electronic appliance provided with the control circuits can display various images on a pixel portion 23 by the control circuits controlling lighting and non-lighting or luminance of the light emitting element.

Note that the panel and the module correspond to one mode of a light emitting device of the present invention, and both are included in the scope of the present invention.

A light emitting device of the present invention as described above is a light emitting device having a pixel portion with reduced power consumption and an improved display quality because it includes the light emitting element described in Embodiment Mode 2 which includes the stilbene derivative described in Embodiment Mode 1 in an organic compound containing layer. In addition, a light emitting device of the present invention as described above is a light emitting device with reduced power consumption and an improved display quality because the light emitting device includes the light emitting element described in Embodiment Mode 2 as a light emitting element included in the pixel portion which includes the stilbene derivative described in Embodiment Mode 1 in an organic compound containing layer.

Embodiment Mode 7

A typical example of an electronic appliance of the present invention is described with reference to FIGS. 9A to 9E. An electronic appliance of the present invention has at least either a light emitting element having the stilbene derivative described in Embodiment Mode 1 or the light emitting element described in Embodiment Mode 2, and a control circuit for controlling the light emitting element. As an electronic appliance of the present invention, a video camera, a digital camera, a goggle type display (head-mounted display), a navigation system, a sound reproduction device (such as a car audio component), a computer, a game machine, a portable information terminal (such as a mobile computer, a mobile phone, a portable game machine, or an electronic book), an image reproduction device equipped with a recording medium (specifically, a device which reproduces a recording medium such as a digital versatile disc (DVD) and which is equipped with a display for displaying an image), and the like are given.

Figure 9A:
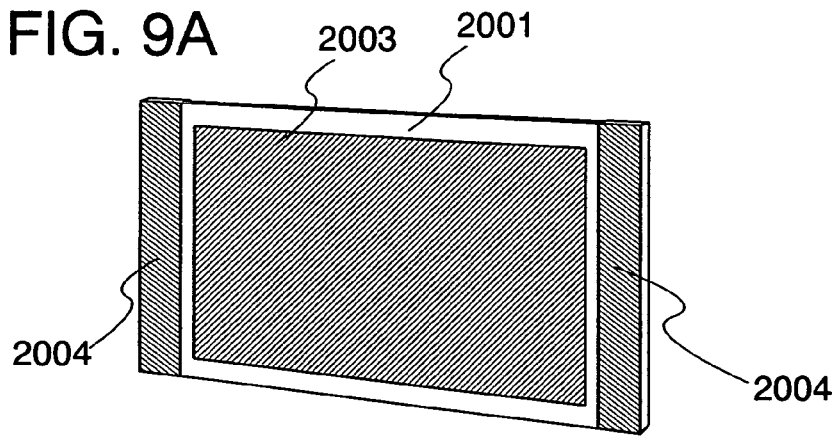
FIGS. 9A to 9E show examples of an electrical appliance to which the present invention can be applied.

FIG. 9A shows a light emitting device which corresponds to a TV receiver, a monitor of a personal computer, or the like. The light emitting device includes a chassis 2001, a display portion 2003, a speaker portion 2004, and the like. A light emitting device of the present invention has reduced power consumption and an improved display quality since the light emitting device has a light emitting element in the display portion 2003 and the light emitting element includes the stilbene derivative described in Embodiment Mode 1 with a large energy gap and an electron transporting property. A pixel portion is preferably provided with a polarizing plate or a circularly polarizing plate to enhance contrast. For example, a quarter-wave plate, a half-wave plate, and a polarizing plate are preferably formed sequentially over a sealing substrate. Further, an anti-reflective film may be provided over the polarizing plate.

Figure 9B:
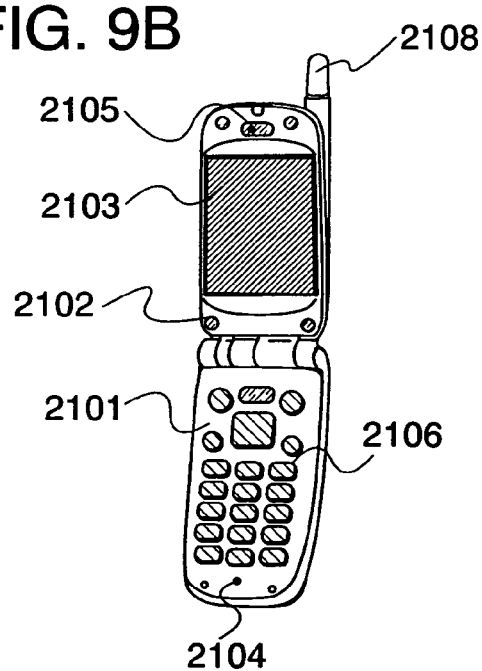

FIG. 9B shows a mobile phone which can be used for watching television, which includes a main body 2101, a chassis 2102, a display portion 2103, an audio input portion 2104, an audio output portion 2105, an operation key 2106, an antenna 2108, and the like. A mobile phone of the present invention has reduced power consumption and an improved display quality since the mobile phone has a light emitting element in the display portion 2103 and the light emitting element includes the stilbene derivative described in Embodiment Mode 1 with a large energy gap and an electron transporting property.

Figure 9C:
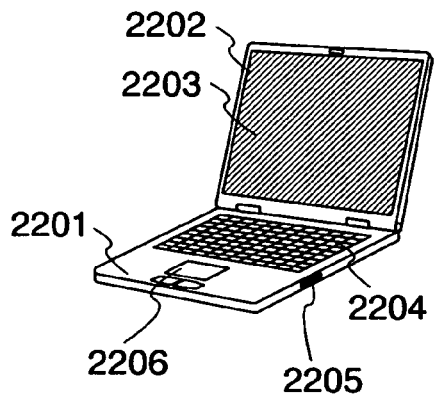

FIG. 9C shows a computer which includes a main body 2201, a chassis 2202, a display portion 2203, a keyboard 2204, an external connection port 2205, a pointing mouse 2206, and the like. A computer of the present invention has reduced power consumption and an improved display quality since the computer has a light emitting element in the display portion 2203 and the light emitting element includes the stilbene derivative described in Embodiment Mode 1 with a large energy gap and an electron transporting property. Although a notebook computer is shown in FIG. 9C as an example, the present invention can also be applied to a desktop computer or the like.

Figure 9D:
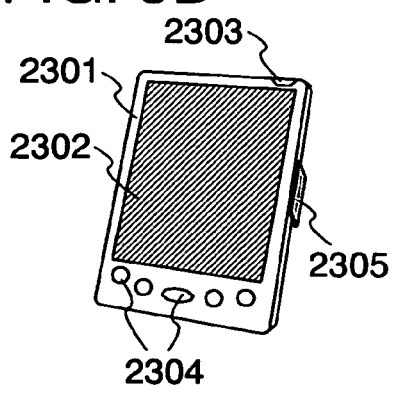

FIG. 9D shows a mobile computer which includes a main body 2301, a display portion 2302, a switch 2303, an operation key 2304, an infrared port 2305, and the like. A mobile computer of the present invention has reduced power consumption and an improved display quality since the mobile computer has a light emitting element in the display portion 2302 and the light emitting element includes the stilbene derivative described in Embodiment Mode 1 with a large energy gap and an electron transporting property.

Figure 9E:
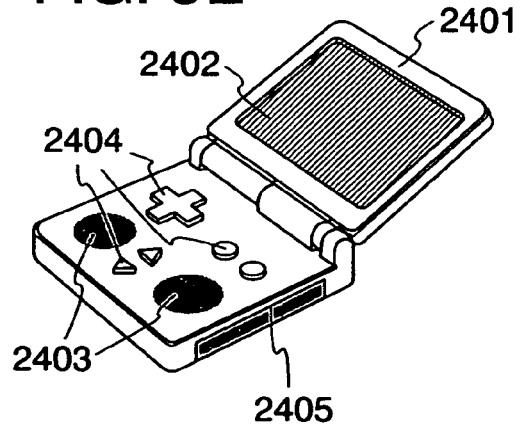

FIG. 9E shows a portable game machine which includes a chassis 2401, a display portion 2402, a speaker portion 2403, an operation key 2404, a recording medium insertion portion 2405, and the like. A portable game machine of the present invention has reduced power consumption and an improved display quality since the portable game machine has a light emitting element in the display portion 2402 and the light emitting element includes the stilbene derivative described in Embodiment Mode 1 with a large energy gap and an electron transporting property.

As described above, an applicable range of the present invention is so wide that the present invention can be applied to electronic appliances of various fields.

This embodiment mode can be combined with structure in Embodiment Modes 1 to 6 arbitrarily.

EXAMPLE 1

Synthesis Example 1

A synthesis method of 3,3'-di(phenanthrene-9-yl)stilbene (DPNS).

A synthesis method of 3,3'-di(phenanthrene-9-yl)stilbene (DPNS) represented by a following structural formula (4), which is a stilbene derivative of the present invention is described.

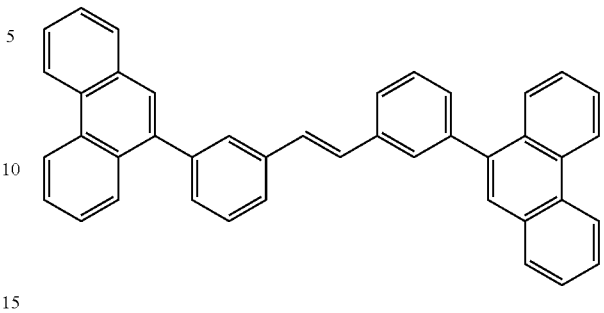

(4)

[Step 1] Synthesis of 3-bromobenzyl triphenylphosphonium bromide.

A 200 mL conical flask was charged with 25.0 g (100.0 mmol) of 3-bromobenzyl bromide and 100 mL of acetone. 27.6 g (105.0 mmol) of triphenylphosphine was added thereto to be stirred for about 24 hours at room temperature. After the reaction, precipitate in the reaction mixture was collected by suction filtration to obtain 45.57 g of white powder of 3-bromobenzyl triphenylphosphonium bromide in a yield of 89%. A synthesis scheme of 3-bromobenzyl triphenylphosphonium bromide is shown below.

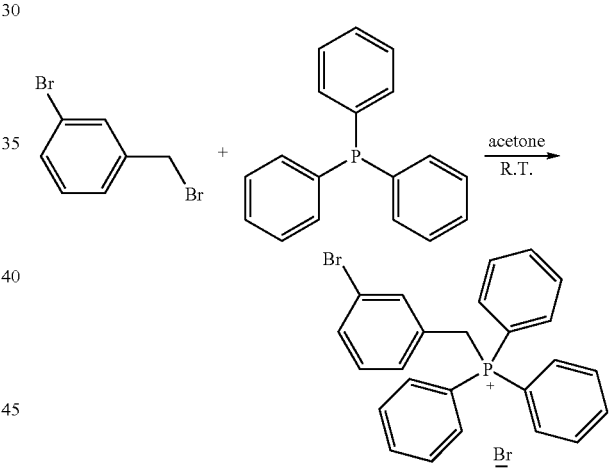

[Step 2] Synthesis of 3,3'-dibromostilbene.

A 500 mL three-neck flask was charged with 22.6 g (44.08 mmol) of 3-bromobenzyl triphenylphosphonium bromide synthesized in Step 1 and 9.79 g (52.90 mmol) of 3-bromobenzaldehyde and the air in the flask was replaced by nitrogen. Then, 150 mL of tetrahydrofuran (THF) was added to the three-neck flask. Thereafter, 5.94 g (52.90 mmol) of tert-butoxy potassium dissolved in 50 mL of THF was dripped into the mixture while being cooled with ice water. Then, the mixture was stirred for about 12 hours at room temperature to cause a reaction. After the reaction, the reaction mixture was washed with water. A water layer was extracted with ethyl acetate and an organic layer was dried with magnesium sulfate. After the drying, the mixture was suction filtrated, and the filtrate was concentrated. The obtained residue was washed with methanol. The solid in the methanol suspension was collected by suction filtration to obtain 5.90 g of white solid of 3,3'-dibromostilbene in a yield of 40%. A synthesis scheme of 3,3'-dibromostilbene is shown below.

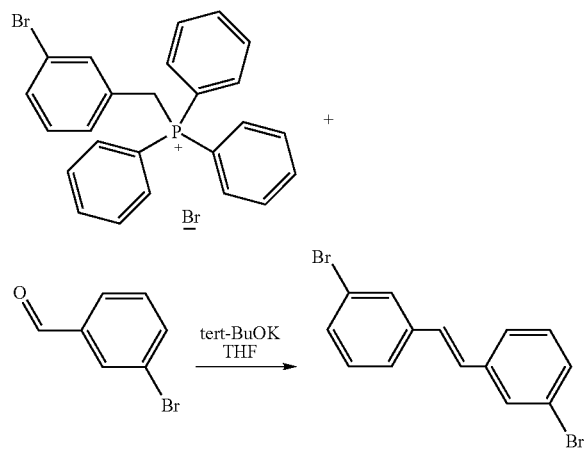

[Step 3] Synthesis of DPNS.

A 100 mL three-neck flask was charged with 1.75 g (5.19 mmol) of 3,3'-dibromostilbene synthesized in Step 2, 2.63 g (11.8 mmol) of 9-phenanthrene boronic acid, 0.023 g (0.103 mmol) of palladium acetate, and 0.221 g (0.727 mmol) of tris(o-tolyl)phosphine, and the air in the flask was replaced by nitrogen. Then, 40 mL of ethylene glycol dimethyl ether and 8 mL (2.0 mol/L) of potassium carbonate aqueous solution were added thereto and stirred for 6 hours at 90° C. to cause a reaction. After the reaction, precipitate in the reaction mixture was collected by suction filtration. After the filtration, the obtained material was recrystallized from chloroform and hexane to obtain 2.11 g of white solid in a yield of 76%. The obtained white solid was identified as DPNS by a nuclear magnetic resonance method (NMR).

Figure 10:
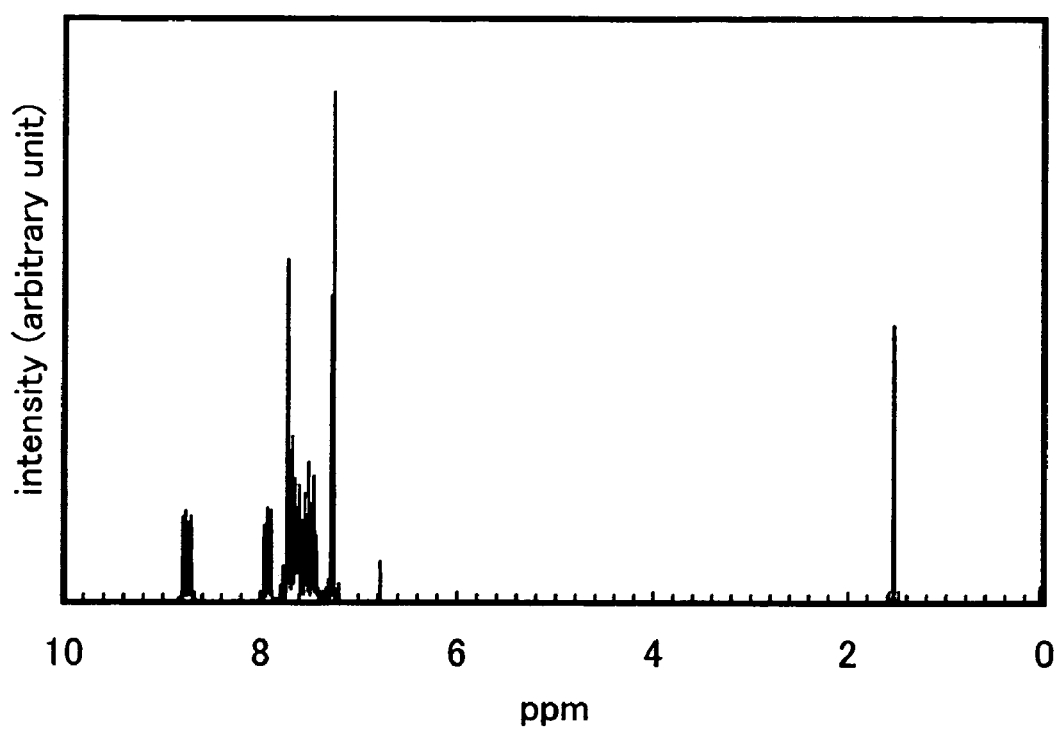
FIG. 10 shows an NMR chart of DPNS.

$^1$H-NMR of the obtained DPNS is shown below. In addition, a $^1$H-NMR chart is shown in FIG. 10.

$^1$H-NMR (300 MHz, CDCl$_3$); δ=8.80-8.72 (m, 4H), 7.96-7.89 (m, 4H), 7.72-7.43 (m, 18H), 7.28 (s, 2H)

A synthesis scheme of DPNS is shown below.

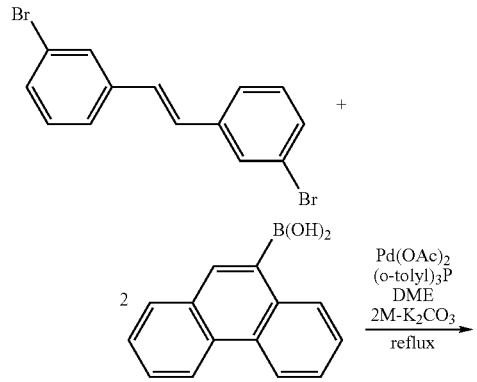

-continued

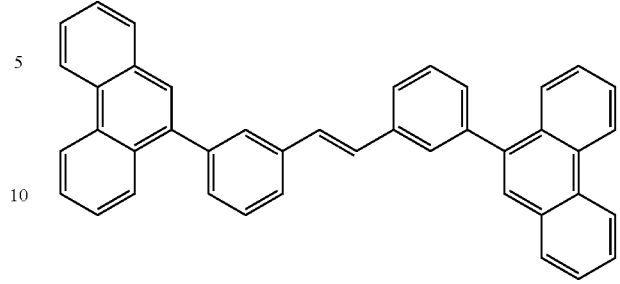

Further, when a decomposition temperature $T_d$ of DPNS was measured by a thermo-gravimetric/differential thermal analyzer (TG/DTA 320, manufactured by Seiko Instruments Inc.), the $T_d$ was 396.4° C. Therefore, it was understood that DPNS has a high $T_d$.

Figure 11:
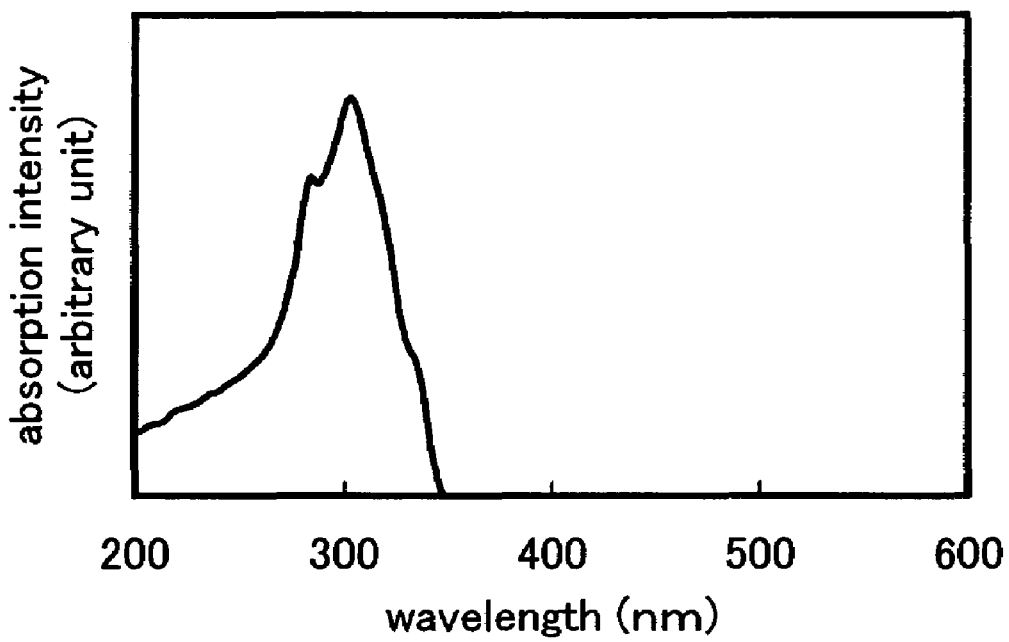
FIG. 11 shows an absorption spectrum of DPNS in a solution state.
Figure 12:
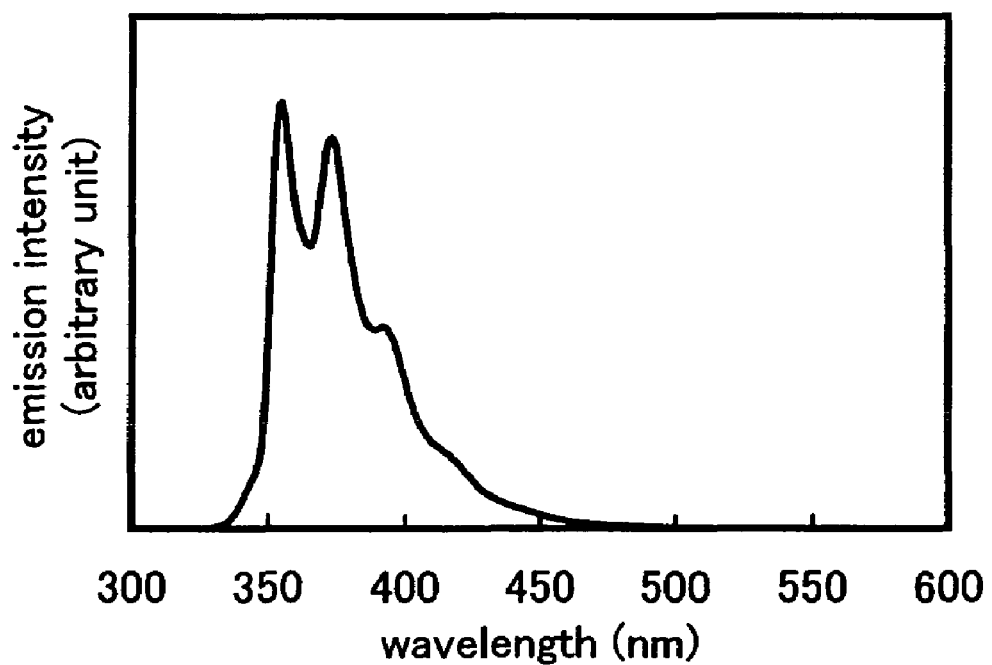
FIG. 12 shows an emission spectrum of DPNS in a solution state.
Figure 13:
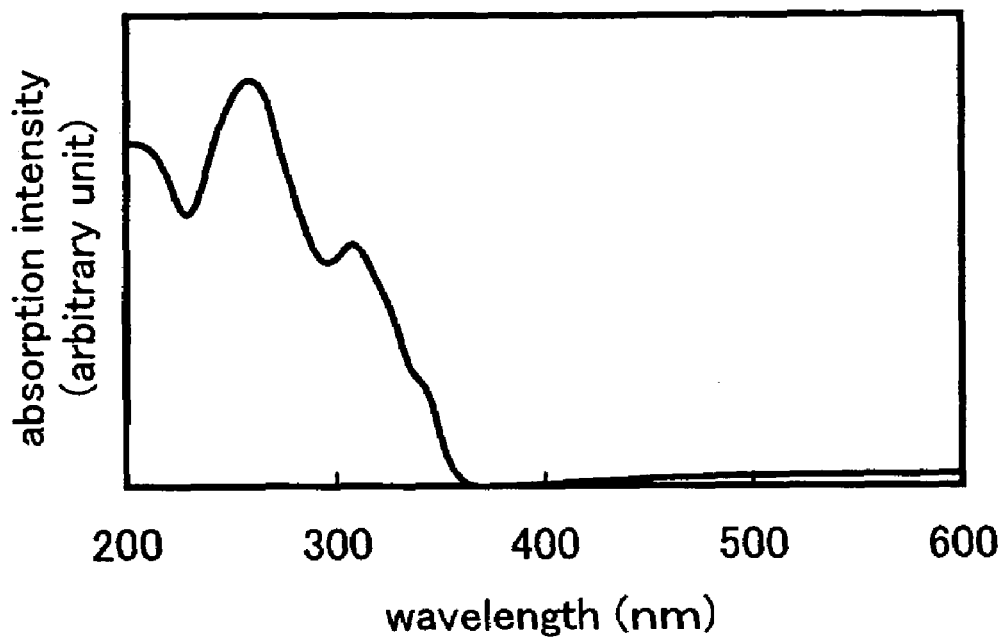
FIG. 13 shows an absorption spectrum of DPNS in a thin film state.
Figure 14:
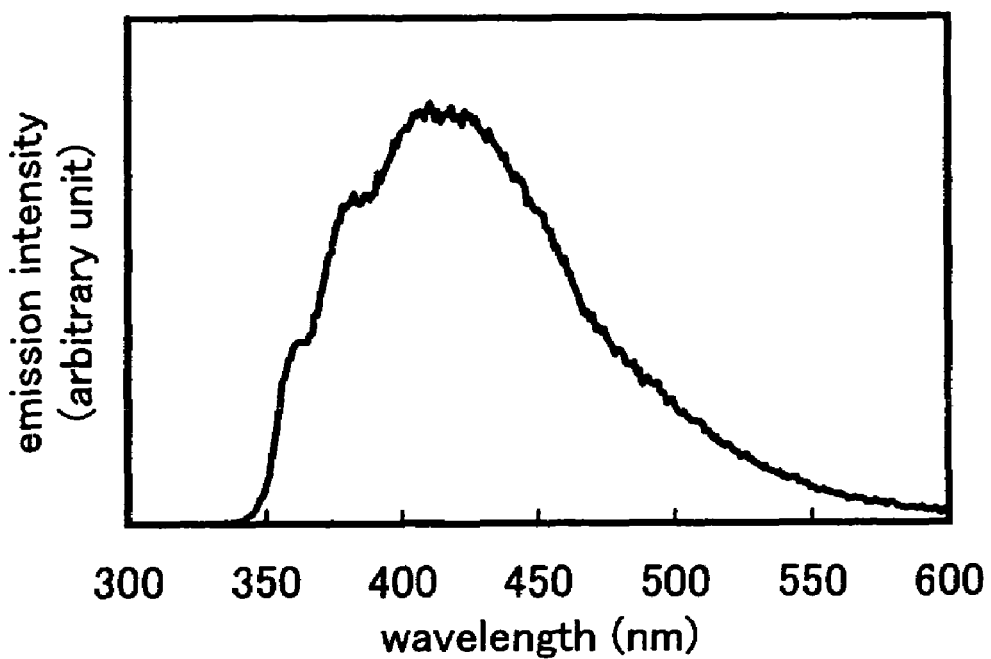
FIG. 14 shows an emission spectrum of DPNS in a thin film state.

An absorption spectrum of DPNS in a state of being dissolved in a toluene solvent is shown in FIG. 11 and that in a thin film state is shown in FIG. 13. An emission spectrum of DPNS in the toluene solution is shown in FIG. 12 and that in the thin film state is shown in FIG. 14. In each of FIGS. 11 and 13, the vertical axis indicates absorption intensity (arbitrary unit) and the horizontal axis indicates wavelength (nm). Also, in each of FIGS. 12 and 14, the vertical axis indicates emission intensity (arbitrary unit) and the horizontal axis indicates wavelength (nm). A light emission from DPNS had peaks at 355 nm and 375 nm (an excited wavelength: 320 nm) in the state of DPNS being dissolved in the toluene solution and had a peak at 410 nm (an excited wavelength: 308 nm) in the state of thin film; therefore, it is understood that blue light emission was obtained.

Using absorption spectrum data in FIG. 13, an absorption edge was obtained from a Tauc plot. Then, the energy at the absorption edge is used as an energy gap and an energy gap of DPNS was found to be 3.5 eV. Since 9,10-diphenylanthracene, which exhibits representative blue emission, has an energy gap of 2.9 eV, it is understood that DPNS has a very large energy gap. Further, the HOMO level in the thin film state was measured by an ambient photoelectron spectroscopy with a spectrometer (AC-2, manufactured by Riken Keiki Co., Ltd.), and was found to be −5.9 eV. Using the HOMO level and the energy gap, the LUMO level was found to be −2.4 eV.

An optimal molecular structure of DPNS in a ground state was calculated using a density functional theory (DFT) at the B3LYP/6-311 (d, p) level. The accuracy of calculation of the DFT is higher than that of a Hartree-Fock (HF) method which neglects electron correlation. In addition, a calculation cost of the DFT is lower than that of a method of perturbation (MP) which has the same level of accuracy of calculation as the DFT. Therefore, the DFT was employed in this calculation. The calculation was performed using a high performance computer (HPC) (Altix3700 DX, manufactured by SGI Japan, Ltd.). From this calculation result, a HOMO level value of DPNS was found to be −5.85 eV.

In addition, singlet excitation energy (energy gap) of DPNS was calculated using a time-dependent density functional theory (TDDFT) at the B3LYP/6-311 (d, p) level of for the molecular structure by the DFT. The singlet excitation energy was calculated to be 3.54 eV.

Synthesis Example 2

A synthesis method of 4,4'-di(phenanthrene-9-yl)stilbene (DPNS2).

A synthesis method of 4,4'-di(phenanthrene-9-yl)stilbene (DPNS2) represented by a following structural formula (5), which is a stilbene derivative of the present invention is described.

(5)

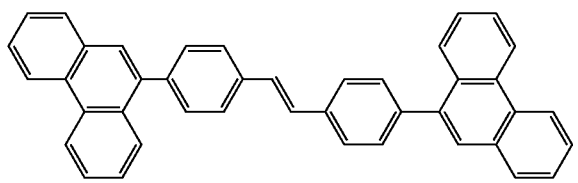

[Step 1] Synthesis of 4-bromobenzyl triphenylphosphonium bromide.

A 200 mL conical flask was charged with 25.36 g (101.5 mmol) of 4-bromobenzyl bromide and 100 mL of acetone. 29.28 g (111.6 mmol) of triphenylphosphine was added thereto to be stirred for about 24 hours at room temperature. After the reaction, precipitate in the reaction mixture was collected by suction filtration to obtain 50 g of white powder of 4-bromobenzyl triphenylphosphonium bromide in a yield of 96%. A synthesis scheme of 4-bromobenzyl triphenylphosphonium bromide is shown below.

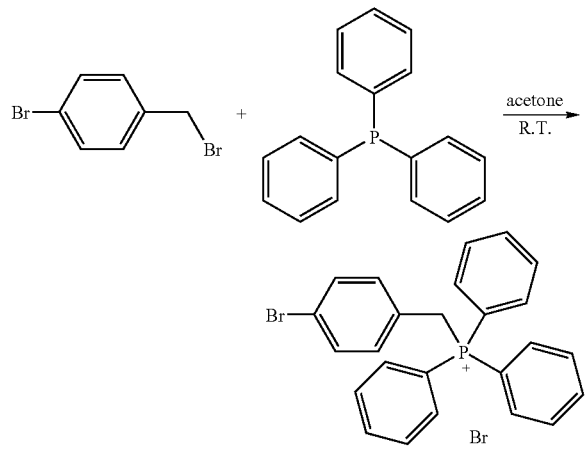

[Step 2] Synthesis of 4,4'-dibromostilbene.

A 1 L three-neck flask was charged with 48.05 g (93.80 mmol) of 4-bromobenzyl triphenylphosphonium bromide synthesized in Step 1 and 20.83 g (112.6 mmol) of 4-bromobenzaldehyde and the air in the flask was replaced by nitrogen. Then, 300 mL of tetrahydrofuran (THF) was added to the three-neck flask. Thereafter, 12.63 g (112.56 mmol) of tert-butoxy potassium dissolved in 100 mL of THF was dripped into the mixture while being cooled with ice water. Then, the mixture was stirred for about 12 hours at room temperature to cause a reaction. After the reaction, the reaction mixture was washed with water. A water layer was extracted with ethyl acetate and an organic layer was dried with magnesium sulfate. After the drying, the mixture was suction filtrated, and the filtrate was concentrated. The obtained residue was washed with methanol. The solid in the methanol suspension was collected by suction filtration to obtain 10.77 g of white solid of 4,4'-dibromostilbene in a yield of 34%. A synthesis scheme of 4,4'-dibromostilbene is shown below.

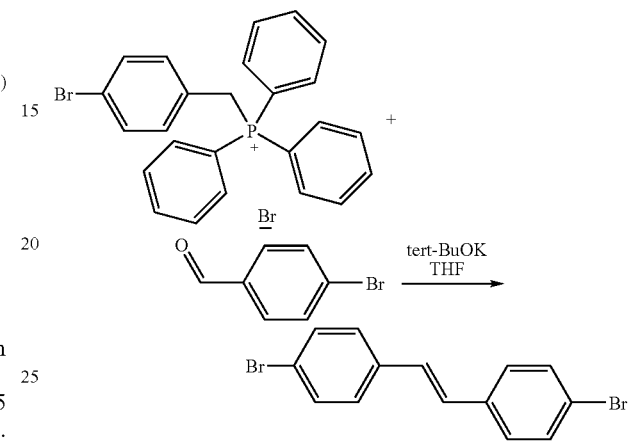

[Step 3] Synthesis of DPNS2.

A 100 mL three-neck flask was charged with 0.80 g (2.37 mmol) of 4,4'-dibromostilbene synthesized in Step 2, 1.2 g (5.40 mmol) of 9-phenanthrene boronic acid, 0.0053 g (0.024 mmol) of palladium acetate, and 0.050 g (0.163 mmol) of tris(o-tolyl)phosphine, and the air in the flask was replaced by nitrogen. Then, 15 mL of ethylene glycol dimethyl ether and 3.5 mL (2.0 mol/L) of potassium carbonate aqueous solution were added thereto and stirred for 8 hours at 90° C. to cause a reaction. After the reaction, precipitate in the reaction mixture was collected by suction filtration. After the filtration, the obtained material was recrystallized from chloroform and hexane to obtain 0.86 g of white solid in a yield of 68%. The obtained white solid was identified as DPNS2 by a nuclear magnetic resonance method (NMR).

Figure 15:
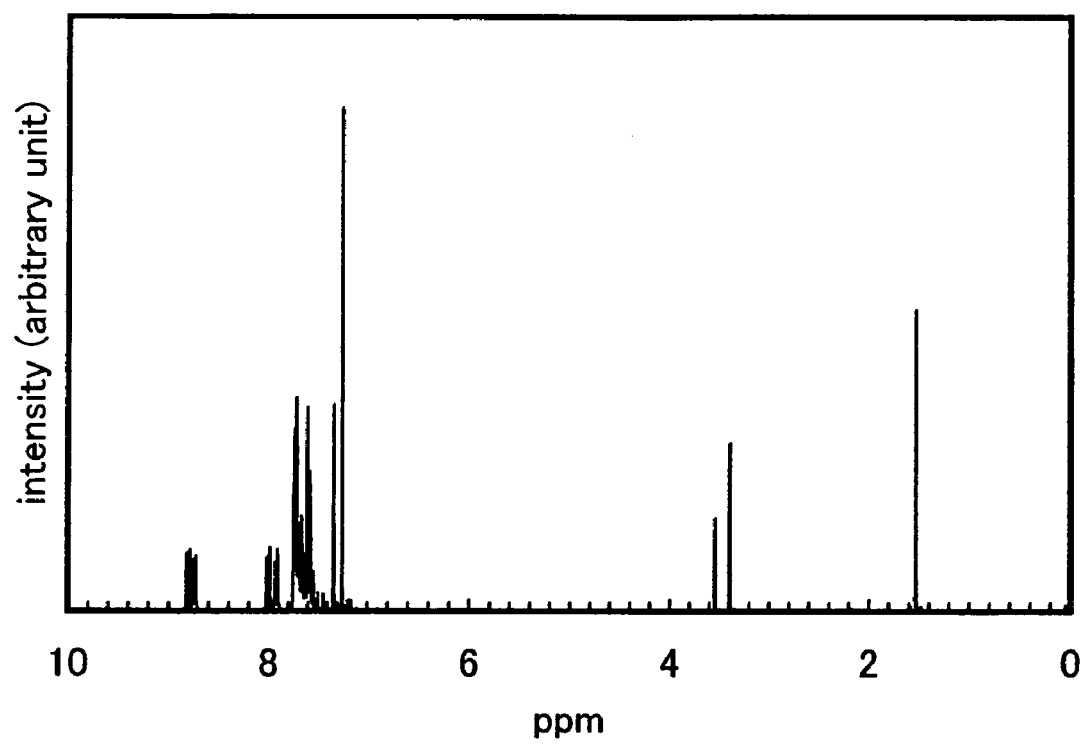
FIG. 15 shows an NMR chart of DPNS2.

$^1$H-NMR of the obtained DPNS2 is shown below. In addition, a $^1$H-NMR chart is shown in FIG. 15.

$^1$H-NMR (300 MHz, CDCl$_3$); δ=8.81-8.73 (m, 4H), 8.02-7.91 (m, 4H), 7.74-7.57 (m, 18H), 7.34 (s, 2H)

A synthesis scheme of DPNS2 is shown below.

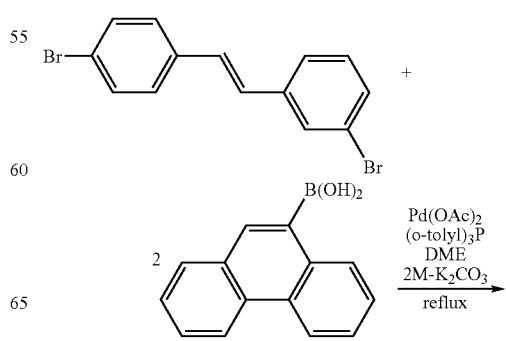

-continued

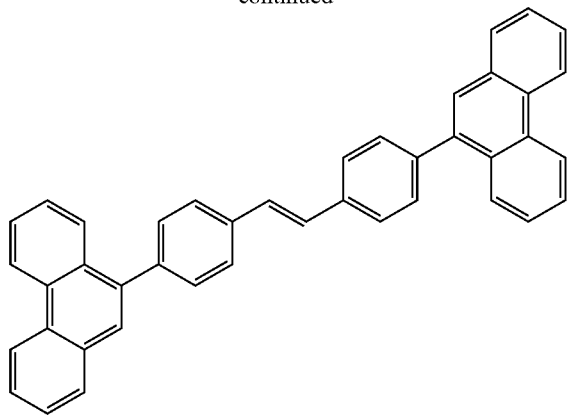

Further, when a decomposition temperature $T_d$ of DPNS2 was measured by a thermo-gravimetric/differential thermal analyzer (TG/DTA 320, manufactured by Seiko Instruments Inc.), the $T_d$ was 416.6° C. Therefore, it was understood that DPNS2 has a high $T_d$.

Figure 16:
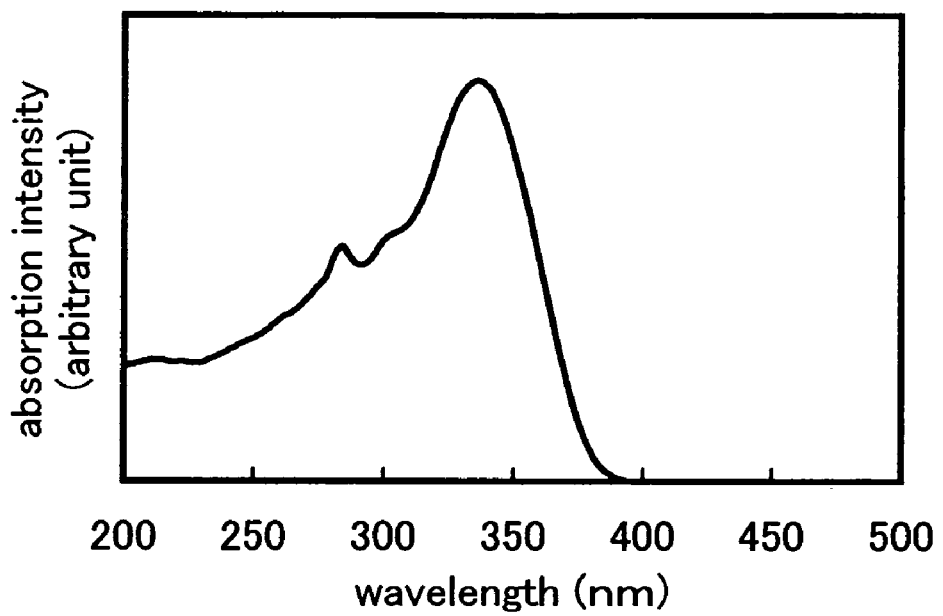
FIG. 16 shows an absorption spectrum of DPNS2 in a solution state.
Figure 17:
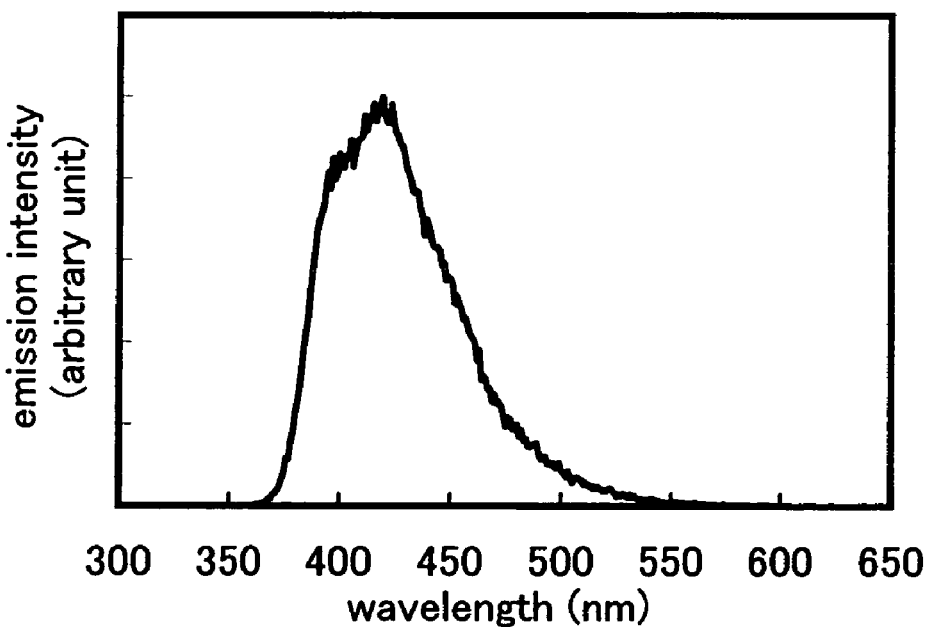
FIG. 17 shows an emission spectrum of DPNS2 in a solution state.
Figure 18:
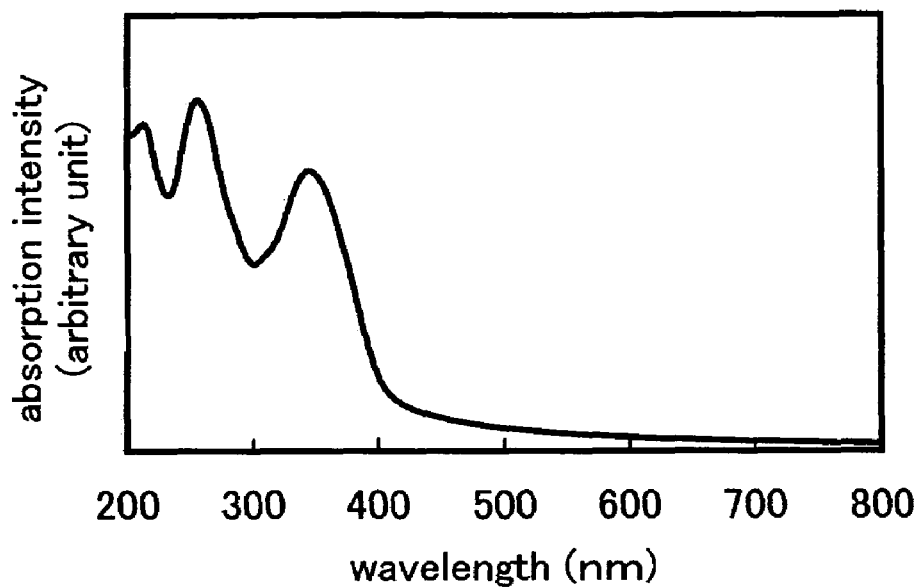
FIG. 18 shows an absorption spectrum of DPNS2 in a thin film state.
Figure 19:
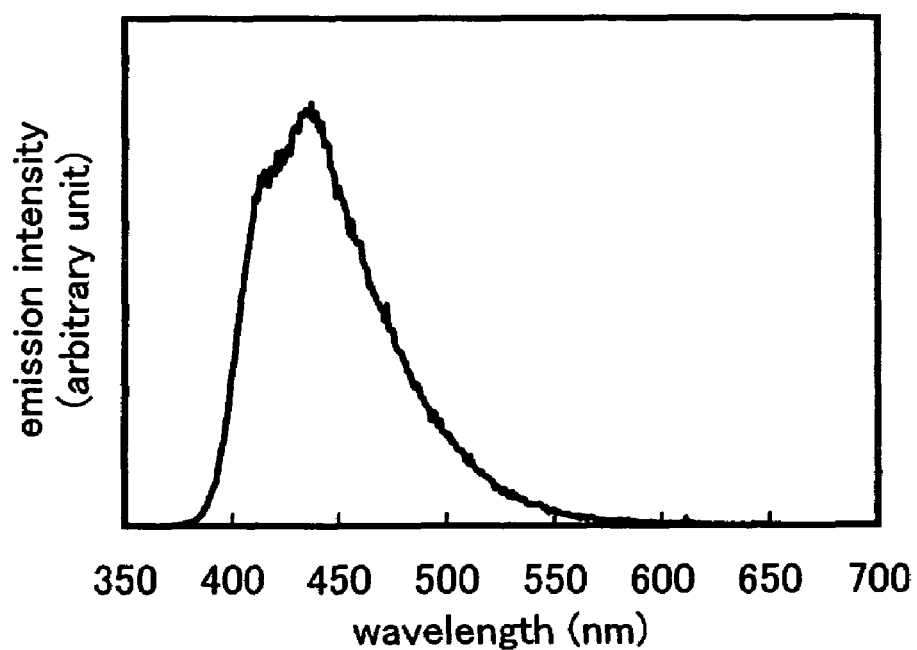
FIG. 19 shows an emission spectrum of DPNS2 in a thin film state.

An absorption spectrum of DPNS2 in a state of being dissolved in a toluene solvent is shown in FIG. 16 and that in a thin film state is shown in FIG. 18. An emission spectrum of DPNS2 in the toluene solution is shown in FIG. 17 and that in the thin film state is shown in FIG. 19. In each of FIGS. 16 and 18, the vertical axis indicates absorption intensity (arbitrary unit) and the horizontal axis indicates wavelength (nm). Also, in each of FIGS. 17 and 19, the vertical axis indicates emission intensity (arbitrary unit) and the horizontal axis indicates wavelength (nm). A light emission from DPNS2 had a peak at 420 nm (an excited wavelength: 348 nm) in the state of DPNS2 being dissolved in the toluene solution and had a peak at 437 nm (an excited wavelength: 344 nm) in a thin film state, therefore, it is understood that blue light emission was obtained.

Using absorption spectrum data in FIG. 18, an absorption edge was obtained from a Tauc plot. Then, the energy at the absorption edge is used as an energy gap and an energy gap of DPNS2 was found to be 3.2 eV. Since 9,10-diphenylanthracene, which exhibits representative blue emission, has an energy gap of 2.9 eV, it is understood that DPNS2 has a very large energy gap. Further, the HOMO level in the thin film state was measured by an ambient photoelectron spectroscopy with a spectrometer (AC-2, manufactured by Riken Keiki Co., Ltd.), and was found to be −5.9 eV. Using the HOMO level and the energy gap, the LUMO level was found to be −2.7 eV.

An optimal molecular structure of DPNS2 in a ground state was calculated by the same method as Synthesis Example 1. From this calculation result, a HOMO level value of the obtained DPNS2 was found to be −5.59 eV.

Singlet excitation energy (energy gap) of DPNS2 was calculated by the same method as Synthesis Example 1. The singlet excitation energy was calculated to be 3.34 eV.

EXAMPLE 2

In this example, a manufacturing method and characteristics of a light emitting element using DPNS as a host material in a light emitting layer are described.

A light emitting element was formed over a glass substrate. An ITSO film was formed as a first electrode to have a thickness of 110 nm in order from the glass substrate side. The ITSO film was formed by a sputtering method. The first electrode was processed into a 2-mm-square in the present invention. Then, a surface of the substrate was washed with a porous resin (typically, made of PVA (polyvinyl alcohol), nylon, or the like) before forming the light emitting element over the first electrode. Then, heat treatment was performed at 200° C. for one hour, and then, UV ozonation was performed for 370 seconds.

Next, a hole injection layer was formed of CuPC to have a thickness of 20 nm. Subsequently, a hole transport layer was formed of BSPB to have a thickness of 40 nm. Over these stacked films, a co-evaporated film was formed of DPNS and TBP as a light emitting layer to have a thickness of 30 nm. A weight ratio of DPNS to TBP was 1:0.01. Then, an electron transport layer was formed of $Alq_3$ to have a thickness of 30 nm and an electron injection layer was formed of calcium fluoride ($CaF_2$) to have a thickness of 1 nm. Lastly, a second electrode was formed of Al to have a thickness of 200 nm. Then, the element was completed. Note that each of the films from the hole injection layer to the second electrode were formed by a vacuum evaporation method by resistance heating.

Figure 20:
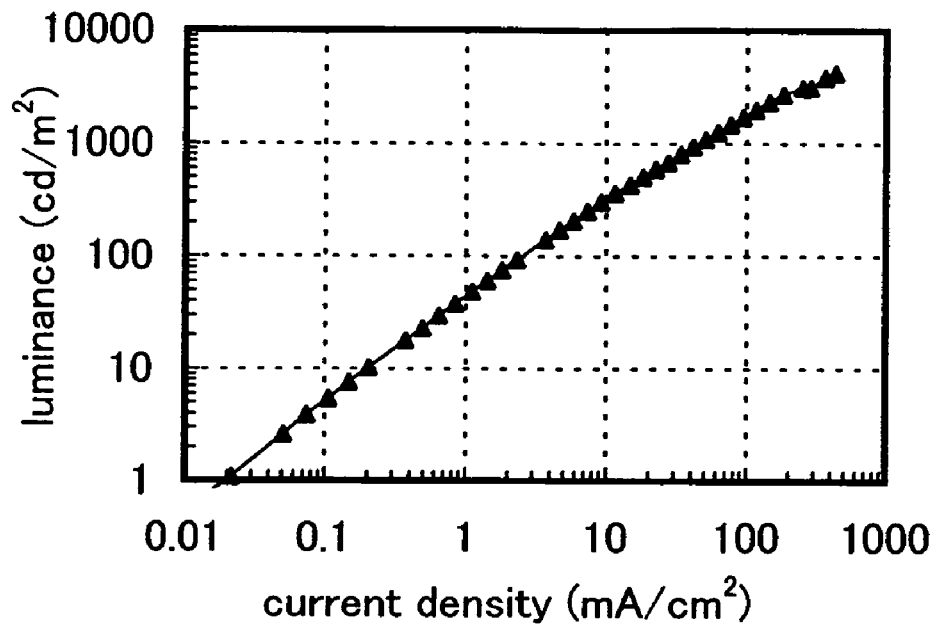
FIG. 20 shows a current density-luminance characteristic of an element using DPNS.
Figure 21:
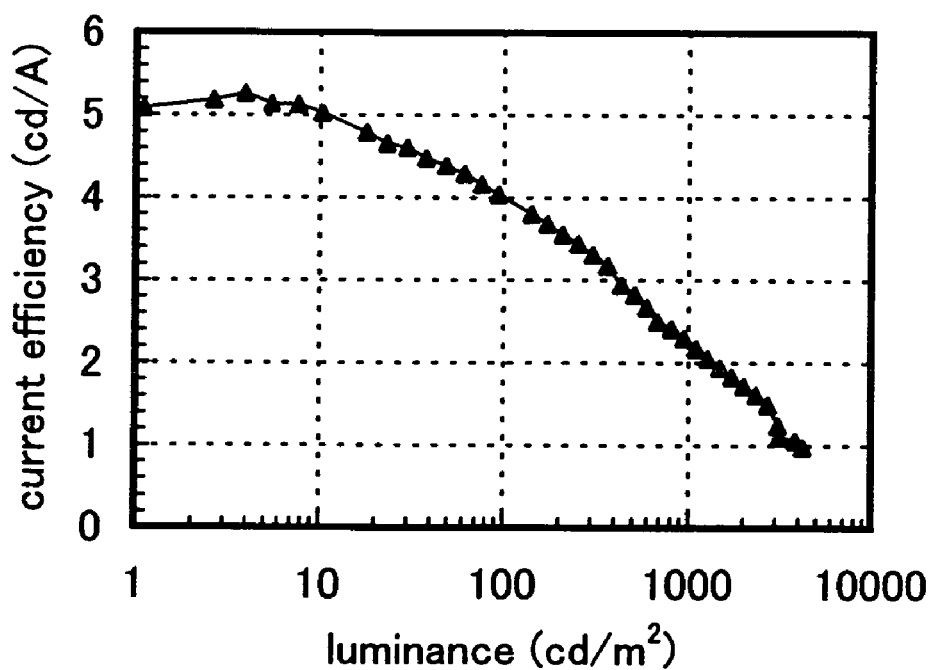
FIG. 21 shows a luminance-current efficiency characteristic of an element using DPNS.
Figure 22:
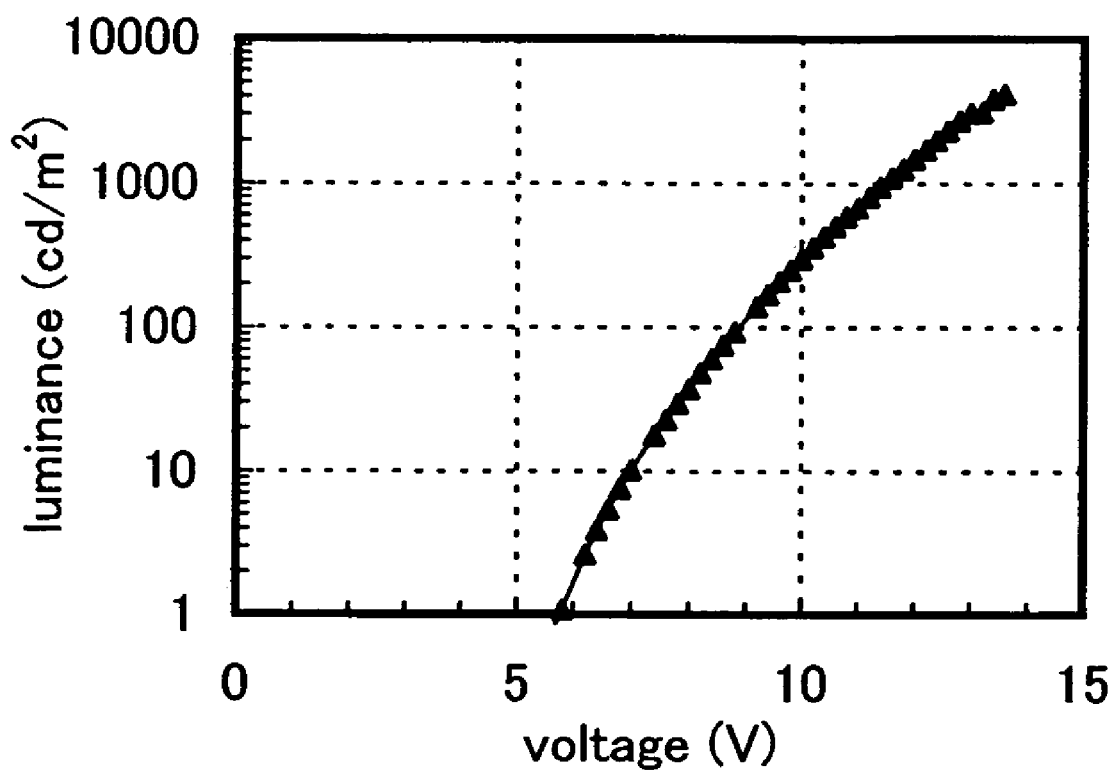
FIG. 22 shows a voltage-luminance characteristic of an element using DPNS.

A current density-luminance characteristic of the formed element is shown in FIG. 20. A luminance-current efficiency characteristic of the formed element is shown in FIG. 21. A voltage-luminance characteristic of the formed element is shown in FIG. 22. In accordance with these characteristics, it is understood that the light emitting element using DPNS which is a stilbene derivative of the present invention emits light with sufficient luminance with low voltage and converts current into light efficiently. That is, it can be said that the light emitting element using DPNS which is a stilbene derivative of the present invention has favorable characteristics. In addition, light emission from the formed element was favorable blue with CIE chromaticity coordinates of (x, y)=(0.15, 0.20).

Note that $Alq_3$ (which exhibits green light emission) which has a smaller energy gap than DPNS was used in the electron transport layer being in contact with the light emitting layer. However, since favorable blue with CIE chromaticity coordinates of (x, y)=(0.15, 0.20) was exhibited, it is understood that $Alq_3$ does not emit light. Accordingly, DPNS does not transport holes, which means that DPNS has an electron transporting property.

As described above, the light emitting element of this example uses DPNS which is the stilbene derivative described in Embodiment Mode 1 as a host material of the light emitting layer. Since the energy gap of DPNS is large, light emission from TBP which is a light emitting material can be efficiently obtained. Accordingly, the light emitting element exhibiting blue light emission with favorable color purity was able to be formed.

In addition, the light emitting element of this example uses DPNS, which is the stilbene derivative described in Embodiment Mode 1 as a host material of the light emitting layer. Since DPNS has an electron transporting property, when $Alq_3$ is used as the electron transport layer, light emission from $Alq_3$ is not caused; therefore, the light emitting element exhibiting blue light emission with favorable color purity can be formed.

EXAMPLE 3

In this example, a manufacturing method and characteristics of a light emitting element using DPNS2 as a host material in a light emitting layer are described.

A light emitting element was formed over a glass substrate. An ITSO film was formed as a first electrode to have a thickness of 110 nm (in order from the glass substrate side). The ITSO film was formed by a sputtering method. The first electrode was processed into a 2-mm-square in the present invention. Then, a surface of the substrate was washed with a porous resin (typically, made of PVA (polyvinyl alcohol), nylon, or the like) before forming the light emitting element over the first electrode. Then, heat treatment was performed at 200° C. for one hour, and then, UV ozonation was performed for 370 seconds.

Next, a hole injection layer was formed of CuPC to have a thickness of 20 nm. Subsequently, a hole transport layer was formed of BSPB to have a thickness of 40 nm. Over these stacked films, a co-evaporated film was formed of DPNS2 and TBP as a light emitting layer to have a thickness of 30 nm. A weight ratio of DPNS2 to TBP was 1:0.01. Then, an electron transport layer was formed of $Alq_3$ to have a thickness of 30 nm and an electron injection layer was formed of calcium fluoride ($CaF_2$) to have a thickness of 1 nm. Lastly, a second electrode was formed of Al to have a thickness of 200 nm. Then, the element was completed. Note that each of the films from the hole injection layer to the second electrode was formed by a vacuum evaporation method by resistance heating.

Figure 23:
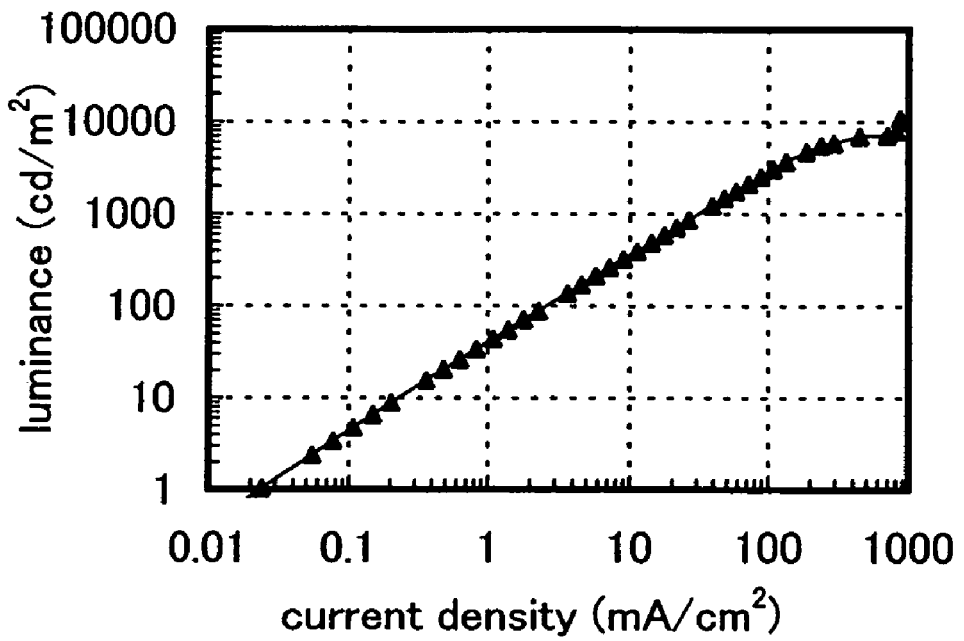
FIG. 23 shows a current density-luminance characteristic of an element using DPNS2.
Figure 24:
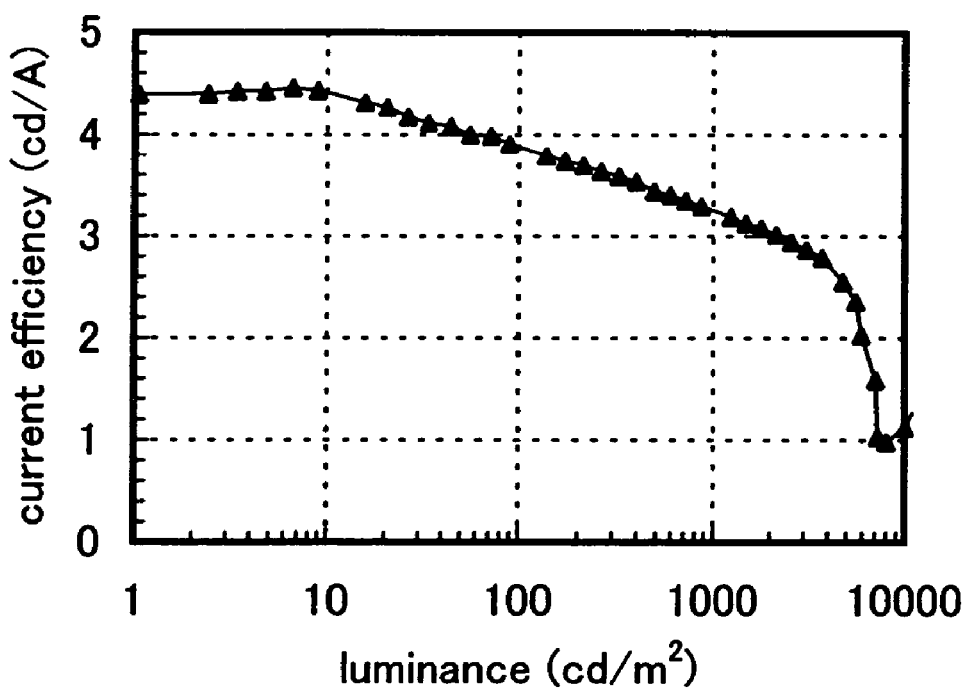
FIG. 24 shows a luminance-current efficiency characteristic of an element using DPNS 2.
Figure 25:
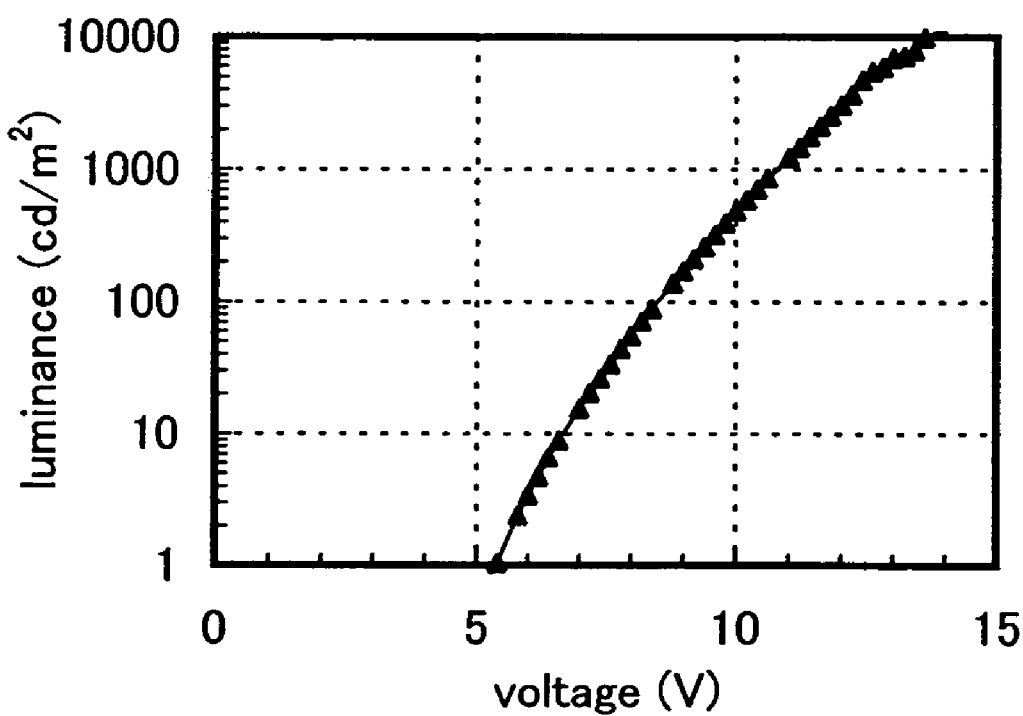
FIG. 25 shows a voltage-luminance characteristic of an element using DPNS2.

A current density-luminance characteristic of the formed element is shown in FIG. 23. A luminance-current efficiency characteristic of the formed element is shown in FIG. 24. A voltage-luminance characteristic of the formed element is shown in FIG. 25. In accordance with these characteristics, it is understood that the light emitting element using DPNS2 which is a stilbene derivative of the present invention emits light with sufficient luminance with low voltage and converts current into light efficiently. That is, it can be said that the light emitting element using DPNS2 which is a stilbene derivative of the present invention has favorable characteristics. In addition, light emission from the formed element was favorable blue with CIE chromaticity coordinates of (x, y)= (0.15, 0.22).

Note that $Alq_3$ (which exhibits green light emission) which has a smaller energy gap than DPNS2 was used in the electron transport layer being in contact with the light emitting layer. However, since favorable blue with CIE chromaticity coordinates of (x, y)=(0.15, 0.22) was exhibited, it is understood that $Alq_3$ does not emit light. Accordingly, DPNS2 does not transport holes, which means that DPNS2 has an electron transporting property.

As described above, the light emitting element of this example uses DPNS2 which is the stilbene derivative described in Embodiment Mode 1 as a host material of a light emitting layer. Since the energy gap of DPNS2 is large, light emission from TBP which is a light emitting material can be efficiently obtained. Accordingly, the light emitting element exhibiting blue light emission with favorable color purity can be formed.

In addition, the light emitting element of this example uses DPNS2 which is the stilbene derivative described in Embodiment Mode 1 as a host material of the light emitting layer. Since DPNS2 has an electron transporting property, when $Alq_3$ is used as an electron transport layer, light emission from $Alq_3$ is not caused; therefore, the light emitting element exhibiting blue light emission with favorable color purity was able to be formed.

This application is based on Japanese Patent Application serial no. 2005-320228 filed in Japan Patent Office on Nov. 3, 2005, the entire contents of which are hereby incorporated by reference.

What is claimed is:

1. A stilbene derivative represented by a following general formula (1),

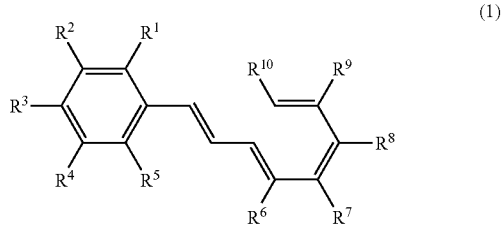

wherein each of $R^1$, $R^2$, $R^3$, $R^4$, and $R^5$ represents hydrogen or a substituent represented by a following structural formula (2), and at least one of $R^1$, $R^2$, $R^3$, $R^4$, and $R^5$ is the substituent represented by the following structural formula (2), and wherein each of $R^6$, $R^7$, $R^8$, $R^9$, and $R^{10}$ represents hydrogen or the substituent represented by the following structural formula (2), and at least one of $R^6$, $R^7$, $R^8$, $R^9$, and $R^{10}$ is the substituent represented by the following structural formula (2)

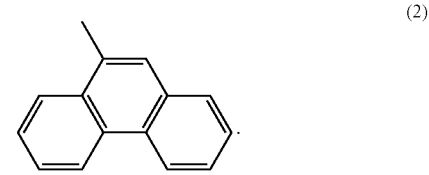

2. A light emitting element material comprising the stilbene derivative according to claim 1.

3. A light emitting element comprising the stilbene derivative according to claim 1.

4. An electronic device having a light emitting element which comprises the stilbene derivative according to claim 1.

5. The stilbene derivative according to claim 1, wherein the stilbene derivative is a host material in a light emitting layer.

6. A stilbene derivative represented by a following general formula (3),

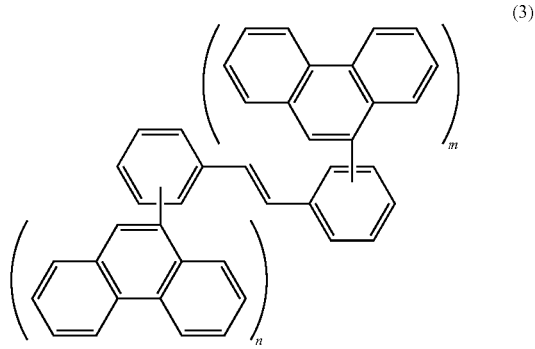

wherein n is an integer of 0, 1 or 2 and m is an integer of 1 or 2.

7. A light emitting element material comprising the stilbene derivative according to claim 6.

8. A light emitting element comprising the stilbene derivative according to claim 6.

9. An electronic device having a light emitting element which comprises the stilbene derivative according to claim 6.

10. The stilbene derivative according to claim 6, wherein the stilbene derivative is a host material in a light emitting layer.

11. A stilbene derivative represented by a following structural formula (4)

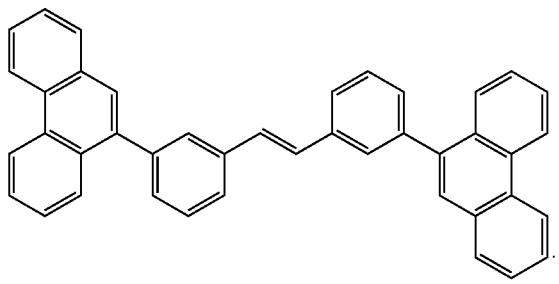

(4)

12. A light emitting element material comprising the stilbene derivative according to claim 11.

13. A light emitting element comprising the stilbene derivative according to claim 11.

14. An electronic device having a light emitting element which comprises the stilbene derivative according to claim 11.

15. The stilbene derivative according to claim 11, wherein the stilbene derivative is a host material in a light emitting layer.

16. A stilbene derivative represented by a following structural formula (5)

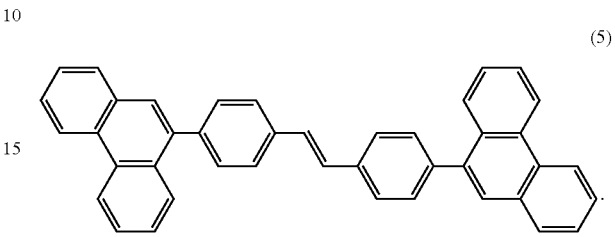

(5)

17. A light emitting element material comprising the stilbene derivative according to claim 16.

18. A light emitting element comprising the stilbene derivative according to claim 16.

19. An electronic device having a light emitting element which comprises the stilbene derivative according to claim 16.

20. The stilbene derivative according to claim 16, wherein the stilbene derivative is a host material in a light emitting layer.

* * * * *

UNITED STATES PATENT AND TRADEMARK OFFICE
CERTIFICATE OF CORRECTION

PATENT NO. : 7,638,663 B2
APPLICATION NO. : 11/591759
DATED : December 29, 2009
INVENTOR(S) : Egawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 507 days.

Signed and Sealed this

Ninth Day of November, 2010

David J. Kappos
*Director of the United States Patent and Trademark Office*